(12) United States Patent
Aron et al.

(10) Patent No.: US 9,662,266 B2
(45) Date of Patent: May 30, 2017

(54) SYSTEMS AND METHODS FOR THE PREDICTIVE ASSESSMENT AND NEURODEVELOPMENT THERAPY FOR ORAL FEEDING

(71) Applicant: Innara Health, Inc., Olathe, KS (US)

(72) Inventors: Kenneth Aron, Olathe, KS (US); David L. Stalling, Olathe, KS (US); John Kean, Olathe, KS (US); Allen Ingling, Olathe, KS (US)

(73) Assignee: Innara Health, Inc., Olathe, KS (US)

( * ) Notice: Subject to any disclaimer, the term of this patent is extended or adjusted under 35 U.S.C. 154(b) by 128 days.

(21) Appl. No.: 14/160,270

(22) Filed: Jan. 21, 2014

(65) Prior Publication Data
US 2014/0134585 A1 May 15, 2014

Related U.S. Application Data

(63) Continuation-in-part of application No. PCT/US2013/038410, filed on Apr. 26, 2013, which
(Continued)

(51) Int. Cl.
*A61B 5/103* (2006.01)
*A61H 7/00* (2006.01)
(Continued)

(52) U.S. Cl.
CPC ......... *A61H 9/0007* (2013.01); *A61B 5/0053* (2013.01); *A61B 5/038* (2013.01);
(Continued)

(58) Field of Classification Search
CPC ............... A61B 5/103; A61J 7/00; A61H 7/00
(Continued)

(56) References Cited

U.S. PATENT DOCUMENTS 4,232,687 A 11/1980 Anderson-Shanklin
5,830,235 A 11/1998 Standley
(Continued)

FOREIGN PATENT DOCUMENTS

CN 101080195 B1 11/2012
EP 1786319 B1 10/2012
(Continued)

OTHER PUBLICATIONS

Barlow et al, "Synthetic orocutaneous stimulation entrains preterm infants with feeding difficulties to suck." J Perinatol, 2008, pp. 541-548, vol. 28, No. 8.
(Continued)

*Primary Examiner* — Carl H Layno
*Assistant Examiner* — Jon Eric C Morales
(74) *Attorney, Agent, or Firm* — Polsinelli PC

(57) ABSTRACT

The present disclosure relates to a therapeutic system and methods of using the therapeutic system. In particular, the present disclosure relates to a system for improving an oral feeding ability of a patient including an assessment device to contact a patient and collect data related to an oral feeding ability of the patient, a computing device containing a processor to execute an assessment and therapy application, and the assessment and therapy application to receive the data related to the oral feeding ability, predict one or more areas of neurological muscle activity that need further development, and develop a neurological therapy treatment for improving the one or more areas of neurological muscle activity that need further development.

18 Claims, 29 Drawing Sheets

Related U.S. Application Data is a continuation of application No. 13/457,059, filed on Apr. 26, 2012, now Pat. No. 8,939,919.

(60) Provisional application No. 61/754,813, filed on Jan. 21, 2013.

(51) Int. Cl.
| | | |
|---|---|---|
| *A61H 9/00* | (2006.01) | |
| *A61N 1/36* | (2006.01) | |
| *A61N 1/372* | (2006.01) | |
| *A61B 5/00* | (2006.01) | |
| *A61B 5/03* | (2006.01) | |
| *A61J 17/00* | (2006.01) | |

(52) U.S. Cl.
CPC .......... *A61B 5/4064* (2013.01); *A61N 1/3606* (2013.01); *A61N 1/37247* (2013.01); *A61B 5/6896* (2013.01); *A61J 17/001* (2015.05); *A61N 1/3611* (2013.01); *A61N 1/3615* (2013.01); *A61N 1/36067* (2013.01); *A61N 1/36103* (2013.01); *A61N 1/36171* (2013.01); *A61N 1/36178* (2013.01)

(58) Field of Classification Search
USPC ......................................................... 600/590
See application file for complete search history.

(56) References Cited

U.S. PATENT DOCUMENTS

| | | | |
|---|---|---|---|
| 6,033,367 | A | 3/2000 | Goldfield |
| 7,435,232 | B2 | 10/2008 | Liebschner |
| 7,917,201 | B2 | 3/2011 | Gozani et al. |
| 8,157,731 | B2 | 4/2012 | Teller et al. |
| 8,226,579 | B2 | 7/2012 | Barlow et al. |
| 8,251,926 | B2 | 8/2012 | Barlow et al. |
| 2004/0019382 | A1 | 1/2004 | Amirouche et al. |
| 2006/0074354 | A1 | 4/2006 | Barlow et al. |
| 2006/0079814 | A1 | 4/2006 | Barlow et al. |
| 2008/0039778 | A1 | 2/2008 | Goldie et al. |
| 2009/0156967 | A1 | 6/2009 | Cohen |
| 2009/0222214 | A1 | 9/2009 | Barlow et al. |
| 2010/0075285 | A1 | 3/2010 | Stalling et al. |
| 2011/0060252 | A1 | 3/2011 | Simonsen et al. |
| 2012/0209147 | A1* | 8/2012 | Barlow et al. ................ 600/590 |
| 2012/0209148 | A1 | 8/2012 | Barlow |

FOREIGN PATENT DOCUMENTS

| | | |
|---|---|---|
| GB | 1206014 A | 9/1970 |
| WO | 2006026623 A2 | 3/2006 |
| WO | 2006081376 A1 | 8/2006 |
| WO | 2008067607 A1 | 6/2008 |

OTHER PUBLICATIONS

Goldfield et al.; "Coordination of Sucking, Swallowing, and Breathing and Oxygen Saturation During Early Infant Breast-feeding and Bottle-feeding"; Pediatric Research; vol. 60;/ No. 4; pp. 450-455; Oct. 2006.

Poore et al., "Respiratory treatment history predicts suck pattern stability in preterm infants." J Neonatal Nurs, 2008, pp. 185-192, vol. 14, No. 6.

European Application Serial No. 09250464.6, Office Action mailed Mar. 22, 2012, 11 pgs.

Estep et al., "Non-Nutritive Suck Parameter in Preterm Infants with RDS." J Neonatal Nurs, 2008, pp. 28-34, vol. 14, No. 1.

Stumm et al., "Respiratory Distress Syndrome Degrades the Fine Structure of the Non-Nutritive Suck In Preterm Infants." J Neonatal Nurs, 2008, pp. 9-16, vol. 14, No. 1.

Vantipalli et al.; Somatosensory entrainment of suck in preterm infants: NTrainer CNL Technical Research Report; 2006; 3:1-23 entire document.

PCT/US2013/038405 International Search Report and Written Opinion mailed Jul. 11, 2013; (10 pages).

PCT/US2013/038410 International Search Report and Written Opinion mailed Jul. 15, 2013 (8 pages).

PCT/US13/38400 International Search Report and Written Opinion mailed Jul. 19, 2013 (15 pages).

Supplementary European Search Report from corresponding EP Application No. 14741014.6, mailed Oct. 12, 2016, pp. 1-5.

* cited by examiner

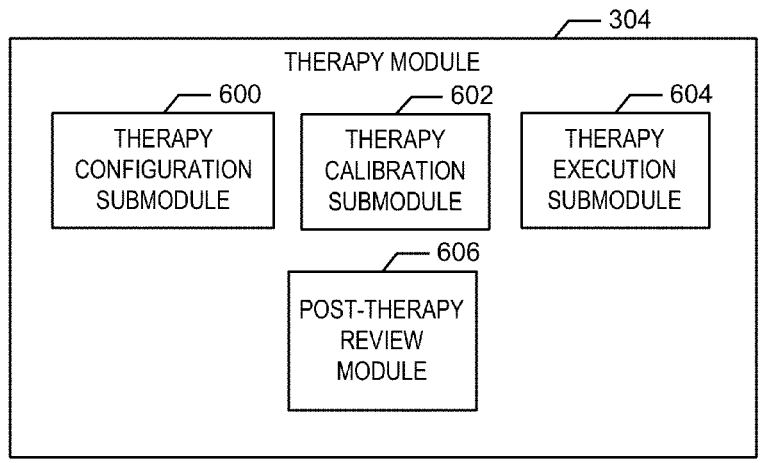
FIG. 6
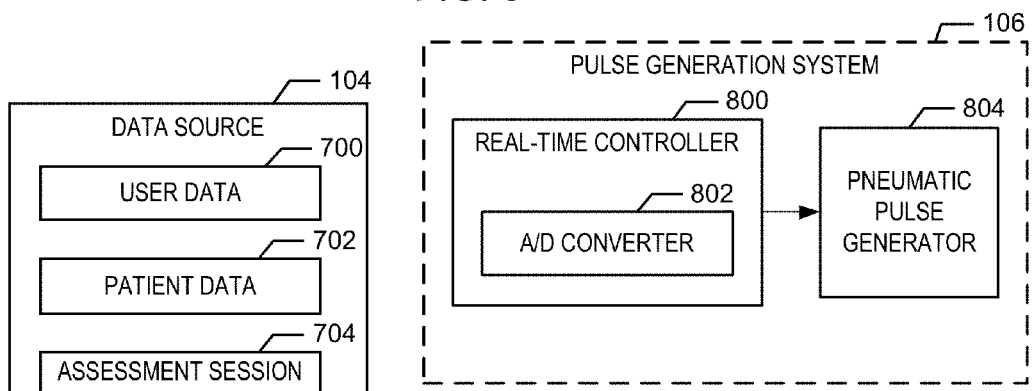
FIG. 8A
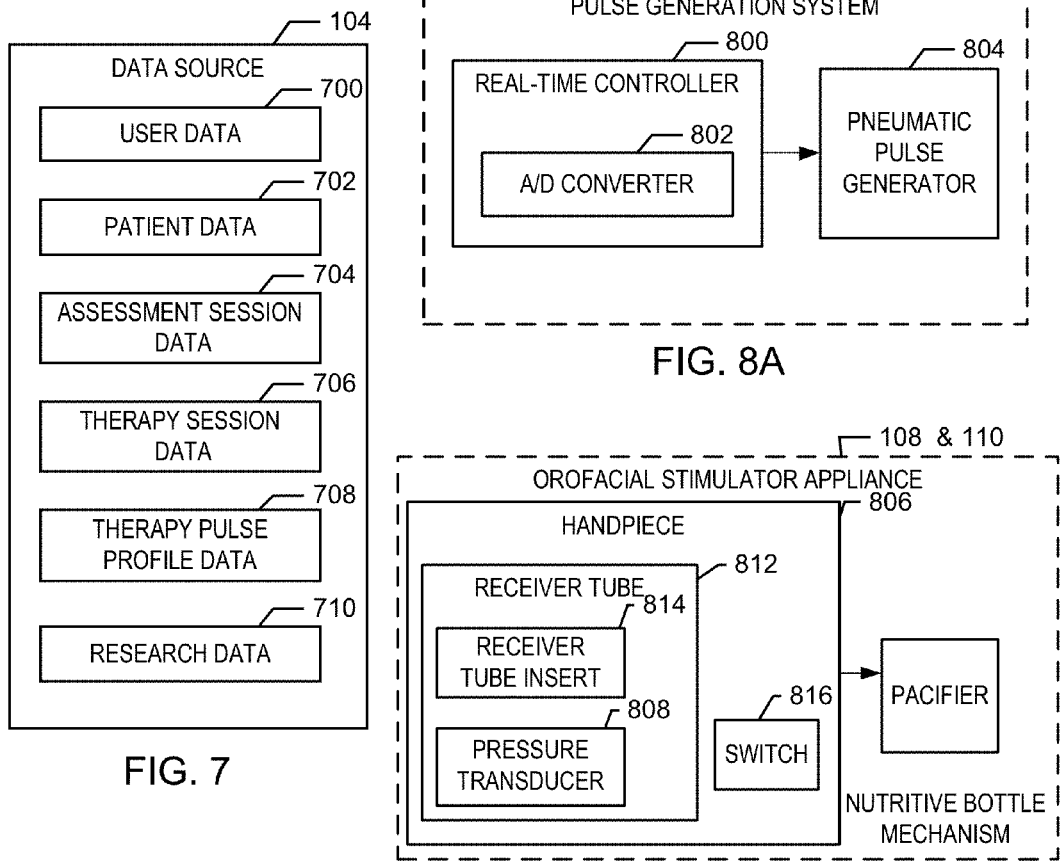
FIG. 7
FIG. 8B

SYSTEMS AND METHODS FOR THE PREDICTIVE ASSESSMENT AND NEURODEVELOPMENT THERAPY FOR ORAL FEEDING

CROSS REFERENCE TO RELATED APPLICATIONS

This application claims priority to U.S. Provisional Application No. 61/754,813 entitled "Systems and Methods for the Predictive Assessment and Neurodevelopment Therapy for Oral Feeding" filed on Jan. 21, 2013, PCT Application No. PCT/US13/38410 entitled "Enhanced Therapeutic Stimulus System and Methods of Use" filed on Apr. 26, 2013, and is a continuation-in-part of U.S. patent application Ser. No. 13/457,059 entitled "Enhanced Therapeutic Stimulus System and Methods of Use" filed on Apr. 26, 2012, all of which are incorporated by reference in their entireties.

FEDERALLY SPONSORED RESEARCH OR DEVELOPMENT

The subject matter discussed in this patent application was funded in part by United States Grant No. R01-DC003311 from the National Institute of Health (NIH). The government may have certain rights to the subject matter discussed herein.

FIELD

The disclosure relates generally to systems and methods for stimulating a central pattern generator and a trigeminal nerve in a brain of a human subject. Specifically, the present disclosure relates to stimulation that influences brain response or brain development including repair of the brain, control of respiration, control of a non-nutritive suck pattern, control of a nutritive suck pattern, mastication, and combinations thereof. Additionally, the disclosure relates to systems and methods to assess and develop the oral feeding capabilities of patients.

BACKGROUND

Premature birth places infants at increased risk for learning disabilities, delayed development of speech, language and motor skills, and mortality. The premature infant often has difficulties with respiration and feeding and therefore may remain in the hospital for prolonged periods of time. The nutritive suck (NS) in a premature infant may be underdeveloped and/or unorganized. A NS is typically used when breastfeeding or bottle-feeding and provides an infant with essential nutrition. The non-nutritive suck (NNS) is a motor behavior that can be observed and used to make inference about brain development and organization in this young population.

It is estimated that approximately 15 million premature infants are born worldwide with approximately 12% of those (500,000) being born in the United States. Studies have shown that approximately 55% of preterm infants have problematic feeding behaviors by 6-18 months of age, while preterm infants are 3.6 times more likely to have feeding problems than full-term infants are at 6 years of age. In addition, patients having congenital heart defects or other neurological disorders may have diminished abilities to feed orally. Moreover, parents of children with feeding problems report increased stress, anxiety and diminished family functioning.

Oral stimulation therapy is a common practice, in which feeding therapists manually apply a stimulation using their fingertip. Manually applying stimulation, however, has a number of drawbacks. One such drawback includes the variance in the amount of motion (amplitude) and rhythm (frequency) from therapist to therapist, or even by the same individual. As a result, extensive and costly training and experience are required for a therapist to be proficient at providing manual stimulation and assessment.

In addition, manual stimulation is given essentially blind, as patients can respond by producing a variety of undesirable motor actions, including but not limited to clenching the jaws, tongue compression, tongue thrusting, or other reactions that may be confused with desirable NNS events or NS events. As such, it can be difficult to determine if the manual stimulation is beneficial to the patient.

Therefore, a need exists for an automated system and method of using the system to assess a patient's natural NNS pattern and to provide precise and beneficial tactile stimulus to correct and organize the patients NNS pattern and a system and method to assess a patient's nutritive suck (NS) pattern to efficiently improve the oral feeding capabilities of patients.

SUMMARY

The present disclosure relates to systems and methods to assess and develop the oral feeding capabilities of patients. In one embodiment, the disclosure relates to systems and methods for the predictive assessment of a patient's oral feeding capability. The predictive assessment is used to determine which of the patient's neurological motor skills (e.g., suck, swallow, breathe, locomotion) need further development for a patient to engage in competent feeding. The predictive assessment may reveal one or more deficiencies of primary suck characteristics that are neurologically controlled. The deficiencies may relate to the regularity and number of individual sucks in individual NNS bursts, the organization of collective suck bursts such that stimulation may be needed to increase a level of central suck pattern generator development, the intensity of effort such that NNS practice or therapy may be needed to gain muscle strength or endurance, or the absence of NNS activity (e.g., immature suck function). In another embodiment, the systems and methods relate to a neurodevelopment therapy that provides biofeedback to assist in the development of neurological motor skills for oral feeding.

The present disclosure further relates to a system having hardware, software, and appliance components for assessing and entraining a behavior in a patient and methods of using the system. In particular, the system relates to the use of specific wave patterns that correspond to action patterns, such that the subject's brain is stimulated. The present disclosure relates to stimulating the central pattern generator of a subject resulting in a developmental response in the orofacial region. In one aspect, the system is used for stimulating a central pattern generator and a trigeminal nerve in a brain of a human subject. The stimulation influences brain response or development of the brain, including but not limited to the repair of the brain, control of respiration, control of a non-nutritive suck pattern, control of a nutritive suck pattern, mastication, and combinations thereof. The system includes an orofacial stimulator appliance that, when actuated in response to a signal, generates a mechanical transfer of energy. The transfer of energy can stimulate the subject's brain. The energy is transferred in at least one burst sufficient to be recognized as a tactile stimulus by the central pattern generator of the brain. Each burst includes at least two square wave pulses of the same amplitude, with the pulse period increasing with each successive pulse to form a decelerating pulse train sequence. The pulses range in frequency between about 1.5 Hz and about 5 Hz. The pulses are contacted with the subject for at least two minutes each day and at least twice a day for a minimum of five successive days. In various embodiments, the use of a square wave is important.

The system also may include a nutritive bottle mechanism that generates a fixed volume or a dynamic volume of nutritive bolus. The nutritive bottle mechanism assesses patient breathing and simulates breastfeeding. The mechanism includes an adaptive flow fluid pump to mimic the flow of breast milk, wherein the pump varies and adapts a volume of the bolus as a function of patient effort.

In one aspect, a system of the present disclosure uses a bi-directional square wave pattern as an input signal to a patient. For example, the square wave pattern may be applied to the patient where it is perceived as an input or feedback signal which then functions as an artificial stimulator of a central pattern generator within the patient's brain. The square wave pattern therefore resonates with the neural system of the patient.

In another aspect, a system is used for stimulating a central pattern generator and a trigeminal nerve in a brain of a subject. The subject may be an adult, an infant, a stroke patient, or other neurologically deficient patients. The stimulation influences brain response or development of the brain, including but not limited to the repair of the brain, control of respiration, control of a non-nutritive suck pattern, control of a nutritive suck pattern, mastication, and combinations thereof. The system includes a control system for generating a pressure pulse signal using a pneumatic pulse generator assembly. Other systems may be used, but a pressure pulse has been shown to be effective. The pneumatic pulse generator assembly can further include a linear motor mechanically engaged to a piston of a pneumatic piston and cylinder assembly, wherein the linear motor exerts force on the piston. The pneumatic piston and cylinder provides a pneumatic pressure pulse to the pliable pacifier through a pneumatic airline in response to the force applied to the piston. The pressure transducer assembly also includes at least one feedback sensor to provide position feedback data and pressure feedback data of the linear motor. Other systems may be used so long as they generate a constant, precise, and modifiable pressure pulse to the subject's mouth and lips. The system further includes, for example, an orofacial stimulator appliance having the pacifier in fluid engagement with a receiver tube. The receiver tube is in fluid communication with the pneumatic airline to provide the pneumatic pressure pulse from the pneumatic piston and cylinder to the pacifier surface. The orofacial stimulator appliance also includes a removable receiver tube insert received in the receiver tube to limit a total volume of air in receiver tube.

The pneumatic pulse generator assembly actuates the orofacial stimulator appliance to generate a mechanical transfer of energy. The energy is transferred in at least one burst sufficient to be recognized as a tactile stimulus recognized by the central pattern generator of the brain. Each burst includes at least two square wave pulses of the same amplitude, with the pulse period increasing with each successive pulse to form a decelerating pulse train sequence. The pulses range in frequency between about 1.5 Hz and about 5 Hz. At least six successive bursts are contacted with the subject for at least two minutes, at least twice daily.

In various aspects, the orofacial stimulator appliance further includes a pneumatic pulse generator having a PID controller and a pump. The orofacial stimulator appliance may also include a piezoelectric system. The orofacial stimulator appliance may also be in communication with a control application executable at a processor. The processor may be a part of a computing device further having a display device and an input device.

The orofacial stimulator applicator may further include a handpiece, a receiver tube, a receiver tube insert, and a pacifier or baglet. In addition, the handpiece may include a push-button switch in communication with the control application.

The PID controller may be a real-time industrial controller, such as a CompactRIO controller. The pump is a linear motor that may further include a position feedback sensor and a pressure feedback sensor. In addition, the pneumatic pulse generator may be a pneumatic piston and cylinder.

In one aspect, each of the two or more pressure pulses includes a damped harmonic of a base frequency. The damped harmonic for the two or more pressure pulses may be identical or vary in frequency. For example, the two or more pressure pulses may have a damped harmonic oscillator profile having a Q factor greater than or equal to ½.

The system may be used to perform various methods for stimulating a central pattern generator and a trigeminal nerve in a human brain of a subject. The stimulation influences brain response or development of the brain, including but not limited to the repair of the brain, control of respiration, control of a non-nutritive suck pattern, control of a nutritive suck pattern, mastication, and combinations thereof. The method includes the steps of contacting the human subject with an appliance to stimulate one or more nerve endings near the subject's mouth, including the facial region proximal to at least one lip and a tongue. The method also includes the steps of actuating the appliance in response to a signal to generate a mechanical transfer of energy. The energy is transferred in at least one burst sufficient to be recognized as a tactile stimulus by the central pattern generator of the brain. Each burst includes at least two square wave pulses of the same amplitude, with the pulse period increasing with each successive pulse to form a decelerating pulse train sequence. The pulses range in frequency between about 1.5 Hz and about 5 Hz.

In various aspects, six bursts of the pulses are contacted with the subject for at least two minutes each day and at least twice a day for a minimum of five successive days. In addition, the square wave pulse may displace a surface of the appliance between about 150 microns and 300 microns or between 260 microns and 300 microns for between about 20 milliseconds and about 50 milliseconds.

In one aspect, the pulses in the burst decelerate. For example, the decelerating pulse train may have period intervals of 510, 526, 551, 580, and 626 ms. Similarly, the pulse spectra may have frequencies of 1.7 Hz, 5.5 Hz, 9.0 Hz, 12, 5 Hz, and 16.5 Hz.

The method may also include the steps of stimulating an olfactory or auditory region of the brain. The method may also include generating or projecting sound waves to generate the square wave pulses. Typically, the tactile stimuli provided by the method are above any background activity of the subject and the signal to generate the mechanical transfer of energy is a high velocity signal. In various aspects, the method may be performed on infants with a heart defect or on stroke patients. Related objects and advantages of the present disclosure will be apparent from the following description.

DESCRIPTION OF FIGURES

FIG. 6 is a block diagram of a therapy module according to one aspect of the therapeutic stimulus system.

FIG. 7 is a block diagram of a data source according to one aspect of the therapeutic stimulus system.

FIG. 8A is a block diagram of a therapeutic pulse generation system according to one aspect of the therapeutic stimulus system.

FIG. 8B is a block diagram of an orofacial stimulator appliance according to one aspect of the therapeutic stimulus system.

FIGS. 12-31 are screenshots of various graphic user interface displays according to aspects of the therapeutic stimulus system.

DETAILED DESCRIPTION

Figure 1:
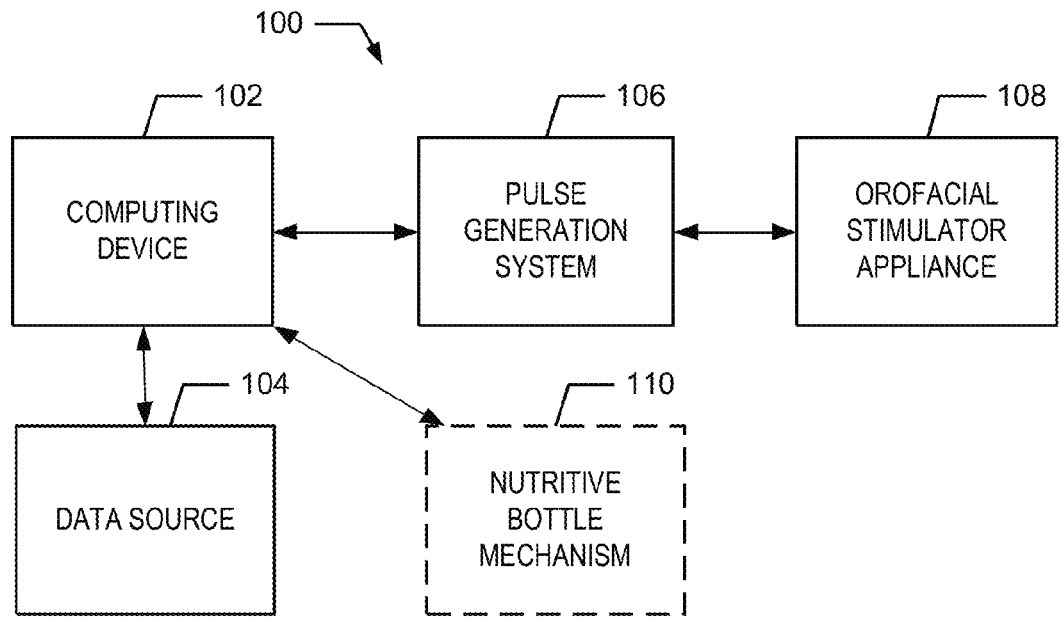
FIG. 1 is a block diagram of a therapeutic stimulus system according to one aspect.

The present disclosure relates to a system for predictive assessment and the neural entrainment of a patient and a system to assess and develop the oral feeding capabilities of a patient. In one aspect, the patient may be a premature infant; however, the system may also be used for patients unable to properly suck or swallow to receive nourishment, including but not limited to full-term infants, toddlers, adolescents, and adults. For example, the system may be used to treat those that have been debilitated by strokes, hemorrhages, heart defects, or other conditions that correlate with an impairment in neurological development or function.

In one aspect, the system of the present disclosure uses a bi-directional square wave pattern as an input signal to a patient. For example, the square wave pattern may be applied to the patient where it is perceived as an input or feedback signal which then functions as an artificial stimulator of a central pattern generator within the patient's brain. The square wave pattern therefore resonates with the neural system of the patient.

The non-nutritive suck (NNS) pattern and nutritive suck pattern (NS) of a patient are generated by the patient's suck central pattern generator (sCPG). A central pattern generator (CPGs) is a neural circuit or combination of neural circuits located in the patient's cerebral cortex, brainstem, and/or spinal cord that drives rhythmic motor behaviors such as sucking, breathing, mastication, and locomotion. The patterns generated by the CPGs can be modulated by a variety of external stimuli, such as the square wave pattern of the present disclosure. In particular, the square wave pattern may be applied to the mouth and lips of a patient where the tongue functions as a high-pass filter to permit components of the square wave pattern matching a natural oscillation pattern of the sCPG to stimulate the patient's sCPG. As such, the most beneficial therapeutic results are manifested when the therapy consistently mimics the intrinsic frequency of sCPG.

It is often difficult for therapists to model the fine temporal structure of an organized NNS burst pattern or NS burst pattern, which involves a frequency-modulated (FM) burst structure, using manual stimulation. The FM burst structure is characterized by a series of suck cycles that successively decrease in frequency from the first compression cycle of the lips and mouth to the last compression cycle. The FM burst structure typically modulates between 1.5 Hz and 3 Hz. The structure of the FM burst is very difficult if not impossible to produce manually in a repeated pattern by even the most experienced therapist.

The present disclosure relates to the identification of particular characteristics of the FM burst structure and provides criteria or descriptions of features of the NNS pattern or NS pattern that may be used as diagnostic indicators for gauging the development of oromotor control among patients. Further, the identified characteristics may be useful in configuring a tactile stimulus that may be applied to patients to modify or correct a deficient NNS pattern or NS pattern.

The Therapeutic Stimulus System

FIG. 1 is a block diagram of a therapeutic stimulus system 100 for assessing a patient's neuromuscular behavior and for providing a tactile stimulus that will stimulate a central pattern generator (CPG) and trigeminal nerve of a human brain to entrain a desired neuromuscular pattern. The therapeutic stimulus system 100 may be used to assess and entrain brain activity for controlling respiration, mastication, other neuromuscular functions, or combinations thereof. For example, the therapeutic stimulus system 100 may be used to treat patients suffering a stroke or other conditions that prevent the patient from performing a desired function. The therapeutic stimulus system 100 includes a computing device 102 to process data and execute one or more applications, a data source 104 to store data, a pulse generation system 106 to generate pneumatic pulses in response to input signals, an orofacial stimulator appliance 108 to transfer the pneumatic pulses to a patient as a tactile stimulus, and an optional nutritive bottle mechanism 110 to provide a nutritive bolus having one of a fixed volume and a dynamic volume to a patient. As an example, the optional nutritive bottle mechanism 110 may be a nutritive suck device for neonate feeding that limits and gates an amount of nutrient fluid available until a patient is in the swallow stage of the suck, swallow, and breathe cycle. An example of the nutritive bottle mechanism 110 is described as nursing device 20 in U.S. Pat. No. 6,033,367 entitled "Smart Bottle and System for Neonatal Nursing Development" filed Aug. 10, 1998 and issued on Mar. 7, 2000, which is incorporated herein by reference in its entirety. However, unlike the smart bottle disclosed in U.S. Pat. No. 6,033,367, various embodiments of the stimulus system 100 and bottle mechanism 110, disclosed herein, provide the benefits of a therapeutic NNS/NS entrainment pattern assisting in the development of a patient's CPG for feeding.

According to one aspect, the therapeutic stimulus system 100 can be used for assessing a patient's natural non-nutritive suck (NNS) pattern or a patient's natural nutritive suck (NS) pattern and for providing a tactile stimulus and/or other stimulus that will stimulate the suck central pattern generator (sCPG) and trigeminal nerve of the patient's brain to entrain a proper NNS pattern or NS pattern. According to another aspect, the therapeutic stimulus system 100 can be used to assess and develop the feeding capabilities of a patient, e.g., for assessing a patient's nutritive suck (NS) pattern. For example, the patients may be neonates, infants who were born prematurely, patients with congenital heart defects, or any other patient with undeveloped and/or under-development motor skills for oral feeding, regardless of age.

Figure 2:
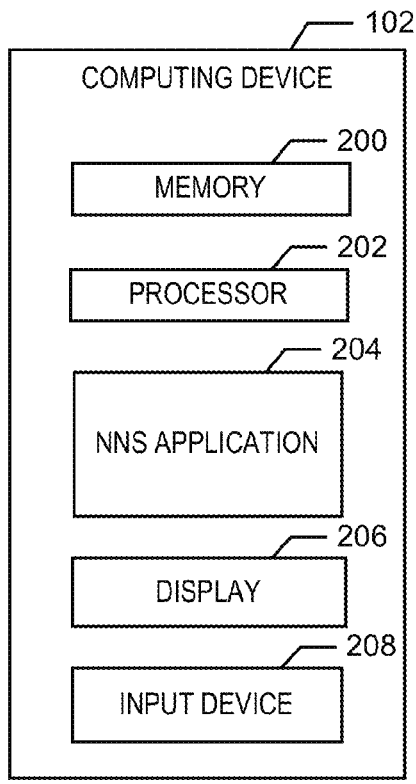
FIG. 2 is a block diagram of computing environment according to one aspect of the therapeutic stimulus system.

By way of example and not limitation, the computing device 102 may include memory 200 and at least one processor 202 to execute a NNS/NS assessment and therapy application (NNS/NS application) 204, as shown in FIG. 2. The computing device 102 also includes a display 206, such as a computer monitor, for displaying data stored in the data source 104, data received from the pulse generation system 106, the orofacial stimulator appliance 108, or the nutritive bottle mechanism 110, and data input by a user of the therapeutic stimulus system 100. The display device 206 also displays one or more graphical user interfaces (GUIs) input forms or displays, generated by the NNS/NS application 204, as shown in FIGS. 12-31. The GUI input forms and displays enable a user of the therapeutic stimulus system 100 to input, view, and/or interact with the various modules of the system. The GUI input forms and displays also allow a user to input, view, and/or interact with patient data, NNS/NS assessment data, NNS/NS therapy data, and/or other data related to the assessment and therapeutic stimulation of the patient. Further, the GUI input forms and displays permit a user to configure and interact with the pulse generation system 106, the orofacial stimulator appliance 108, and the nutritive bottle mechanism 110.

The computing device 102 may also include an input device 208, such as a keyboard or a pointing device (e.g., a mouse, trackball, pen, or touch screen) to enter data or configure a feature of the therapeutic stimulus system 100 using the GUI input forms and displays. The computing device 102 may further include, or at least be in communication with, the data source 104.

The data source 104 may be a database stored on a local hard disk drive (HDD) incorporated into the computing device 102. Alternately, the data source 104 may be a database or other data structure stored remotely from the computing device 102. For example, the computing device 102 may be in communication with the data source 104 over a network, including but not limited to the Internet. As shown in FIG. 7, the data source may store a variety of data. For example, the data source 104 may store user data 700 that includes profiles and login information, such as passwords, for users of the therapeutic stimulus system 100. The data source 104 may also contain patient data 702 including patient charts and historical assessment and therapy session data 704 and 706, respectively. The data source 104 also stores data for therapy protocols or therapy pulse profiles 708 that may be used to entrain a variety of patients, as well as, other data 710 gathered from experiments or research trials conducted using the therapeutic stimulus system 100.

Figure 3:
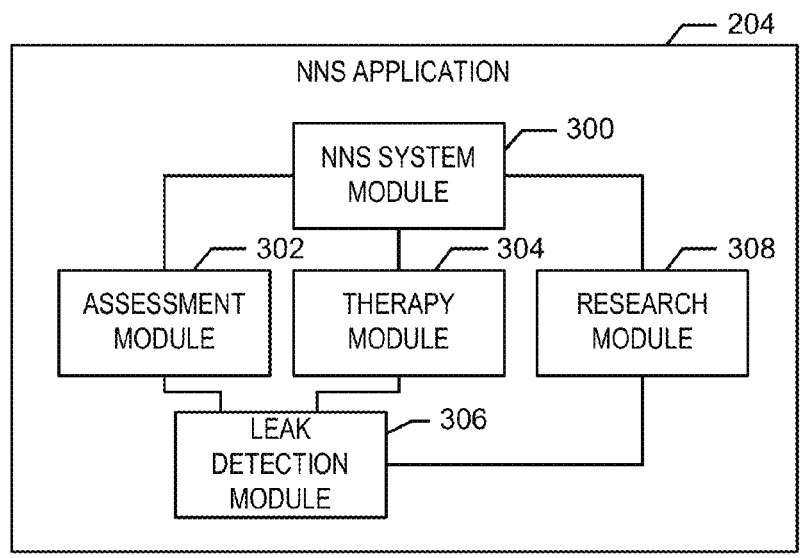
FIG. 3 is a block diagram of a non-nutritive/nutritive suck entrainment application according to one aspect of the therapeutic stimulus system.
Figure 4:
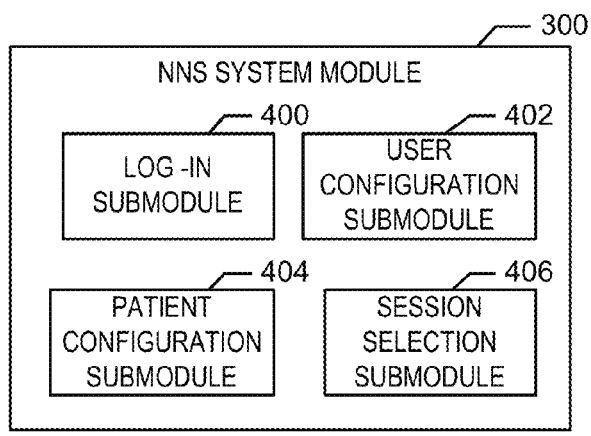
FIG. 4 is a block diagram of a system module according to one aspect of the therapeutic stimulus system.
Figure 5:
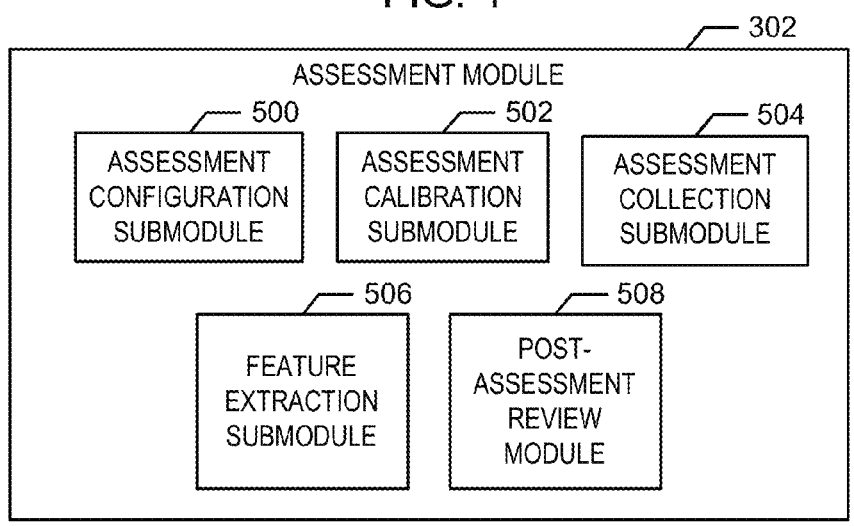
FIG. 5 is a block diagram of an assessment module according to one aspect of the therapeutic stimulus system.
Figure 32:
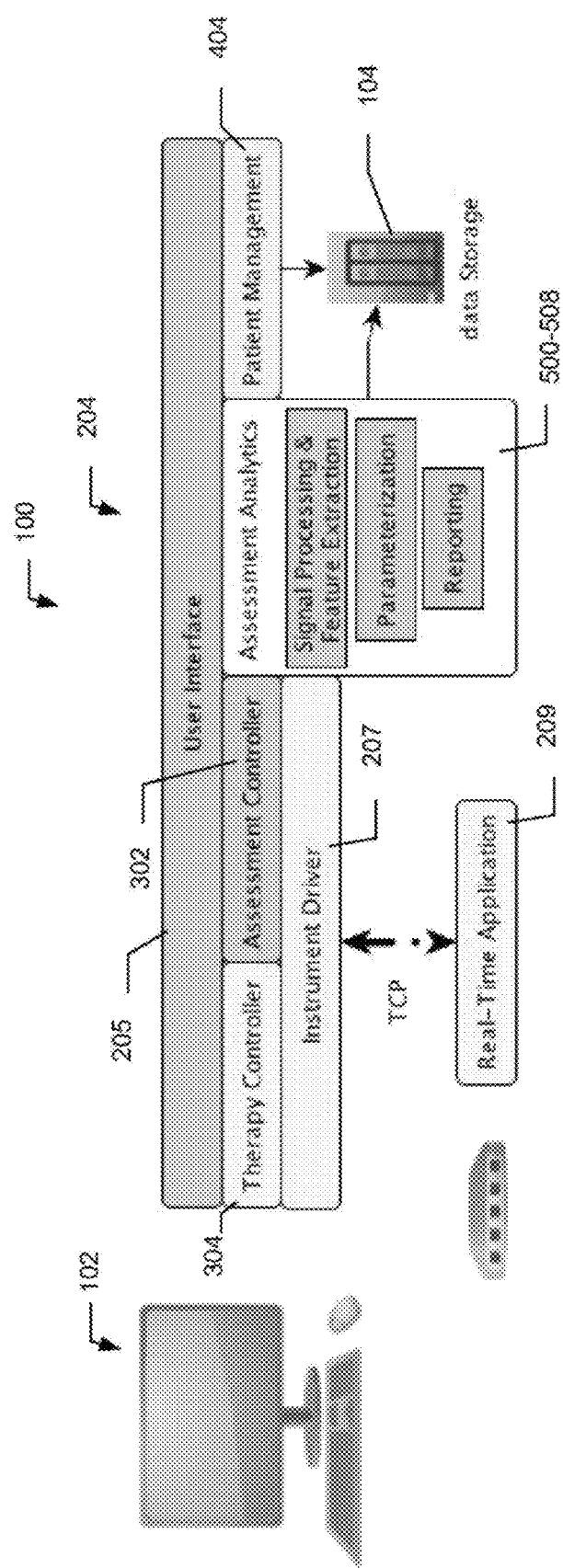
FIG. 32 is an illustration of a software application used in system to predict and improve a patient oral feeding ability according to one aspect.

According to one aspect, as shown in FIG. 3, the NNS/NS assessment and therapy application 204 includes a number of instructions, applets, modules 300-308, and submodules to receive, process, and generate data and/or signals for the assessment of a NNS pattern or NS pattern and the therapeutic stimulation of a patient's mouth and lips to entrain a proper NNS pattern or NS pattern. The modules of the NNS/NS assessment and therapy application 204 include an NNS/NS system module 300, an assessment module 302, a therapy module 304, a leak detection module 306, and a research module 308. The NNS/NS assessment and therapy application 204 also includes an instrument driver 207 that communicates with another instance of the application or another real-time NNS/NS assessment application 209 executing on another computing device 102, as shown in FIG. 32.

According to one embodiment, the real-time assessment application 209 communicates with the NNS/NS assessment and therapy application 204 during prophylactic feeding and determines a burst profile based on a pulse generated by a patient to enforce a non-nutritive or nutritive suck. The NNS/NS assessment and therapy application is continually running on the computing device 102 such that the therapeutic stimulus system is "always on" and ready for use. As such, an assessment may be conducted at any time that the patient may be voluntarily or involuntary attempting an NNS or NS.

According to one other embodiment, the real-time assessment application 209 communicates with the NNS/NS assessment and therapy application 204 to provide a reactive pulse train during assessment of an NNS or NS pattern and provides a therapy stimulus and moderates the stimulus.

According to another aspect, the real-time assessment application 209 communicates with the NNS/NS assessment and therapy application 204 to provide a reactive pulse train during assessment of an NS pattern and a fixed-volume nutritive bolus. The reactive pulse train may be used if the real-time assessment application 209 determines that sucking and swallowing need to be further developed by the patient. As a result, the real-time assessment application 209 provides nutritive, reactive therapy to condition the patient to swallow and breathe properly.

According to an even further aspect, the real-time assessment application 209 communicates with the NNS/NS assessment and therapy application 204 to provide a reactive pulse train during assessment of an NS pattern and adapts a bolus volume as a function of patient effort, requiring the patient to "pull harder" for greater volume, simulating breastfeeding. The adaptive bolus volume is provided by an adaptive-flow fluid pump associated with the nutritive bottle mechanism 110 that mimics a flow of breast, whereby the adaptive-flow fluid pump modifies its volume as a function of effort provided by the patient. The patient effort is defined by a pressure and a nutritive suck activity of the patient, such that the patient must exert greater effort to increase the volume of the bolus. As a result, the real-time assessment application 209 provides nutritive, reactive, and adaptive therapy to condition the patient to swallow and breathe properly. Through the use of the real-time assessment application 209, the patient develops and coordinates a suck, swallow, breathe, and locomotion rhythm.

Figure 12:
Figures 13, 14:

The NNS/NS system module 300 includes various submodules 400-406 to provide access to various features and functionality of the NNS/NS assessment and therapy application 204. For example, the NNS/NS system module 300 includes a user login submodule 400 that allows a user of the therapeutic stimulus system 100 to login to the NNS/NS application 204. In one aspect, the NNS/NS system module 300 generates GUI input forms 1200 and 1202, as shown in FIGS. 12-13, where the user may select a user account and log in to the NNS/NS application 204 after entering a valid password for the selected user.

Figure 15:
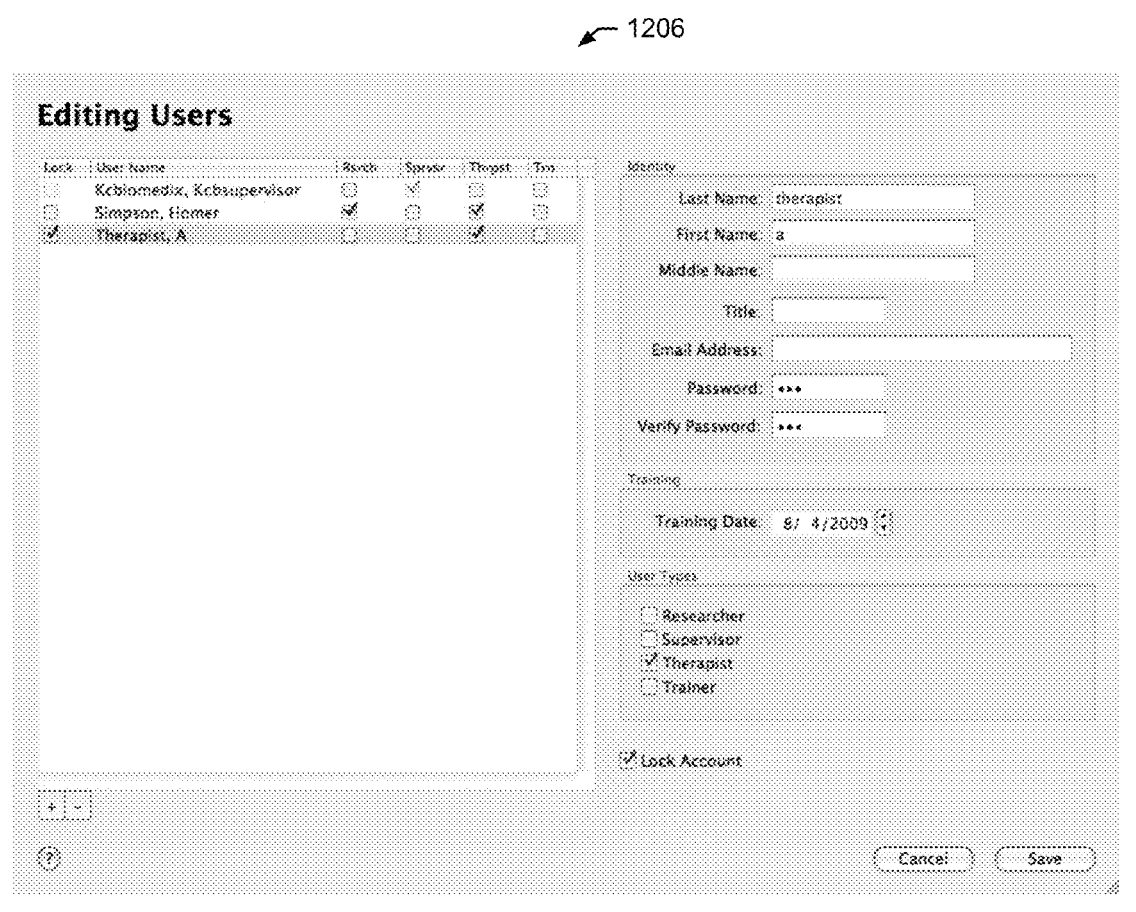

The NNS/NS system module 300 includes a user configuration submodule 402 that allows users of the therapeutic stimulus system 100 with sufficient privileges to add, edit, or delete user accounts. By way of example and not limitation, an administrator may input data into GUI input forms 1204 and 1206, as shown in FIGS. 14-15 to create, modify, or delete a user profile to grant or restrict access to the NNS application 204.

Figure 16:
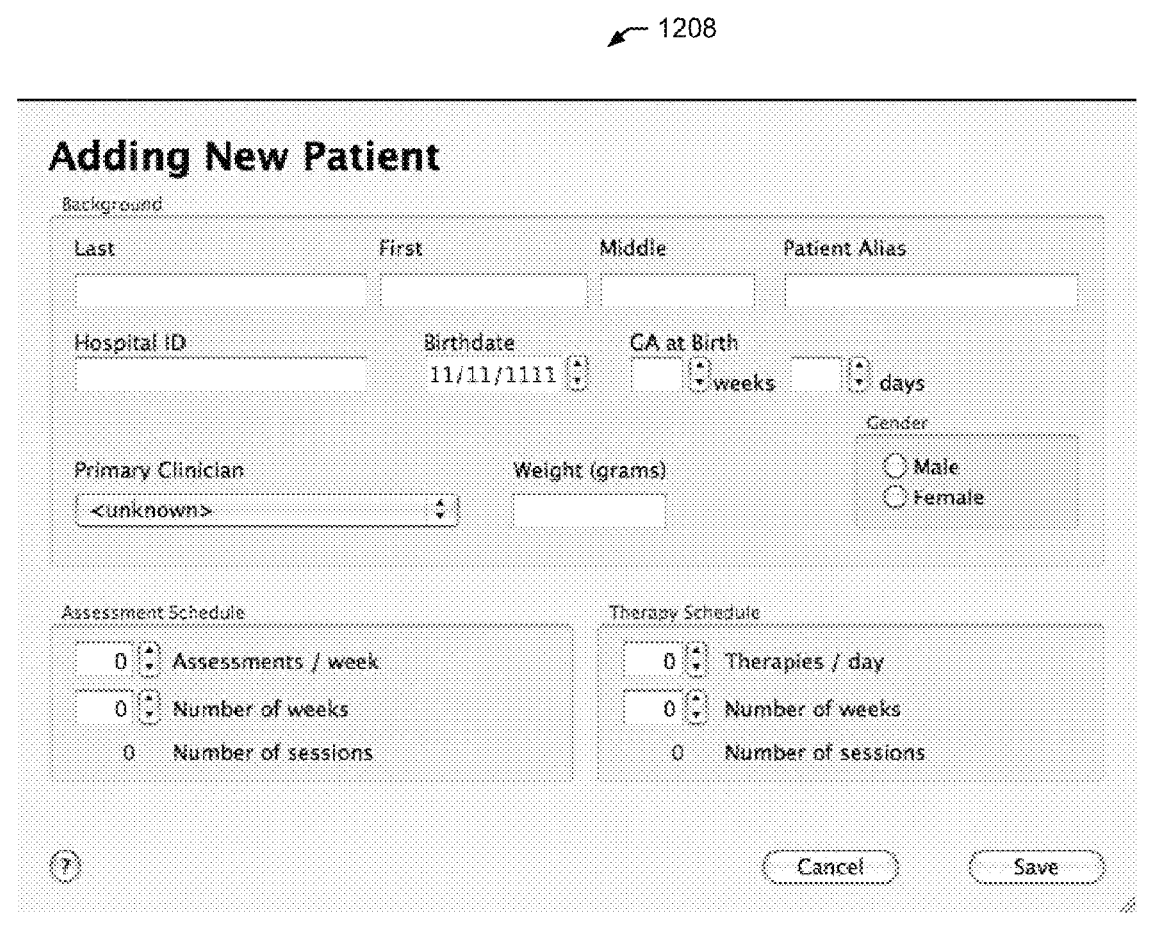
Figure 17:
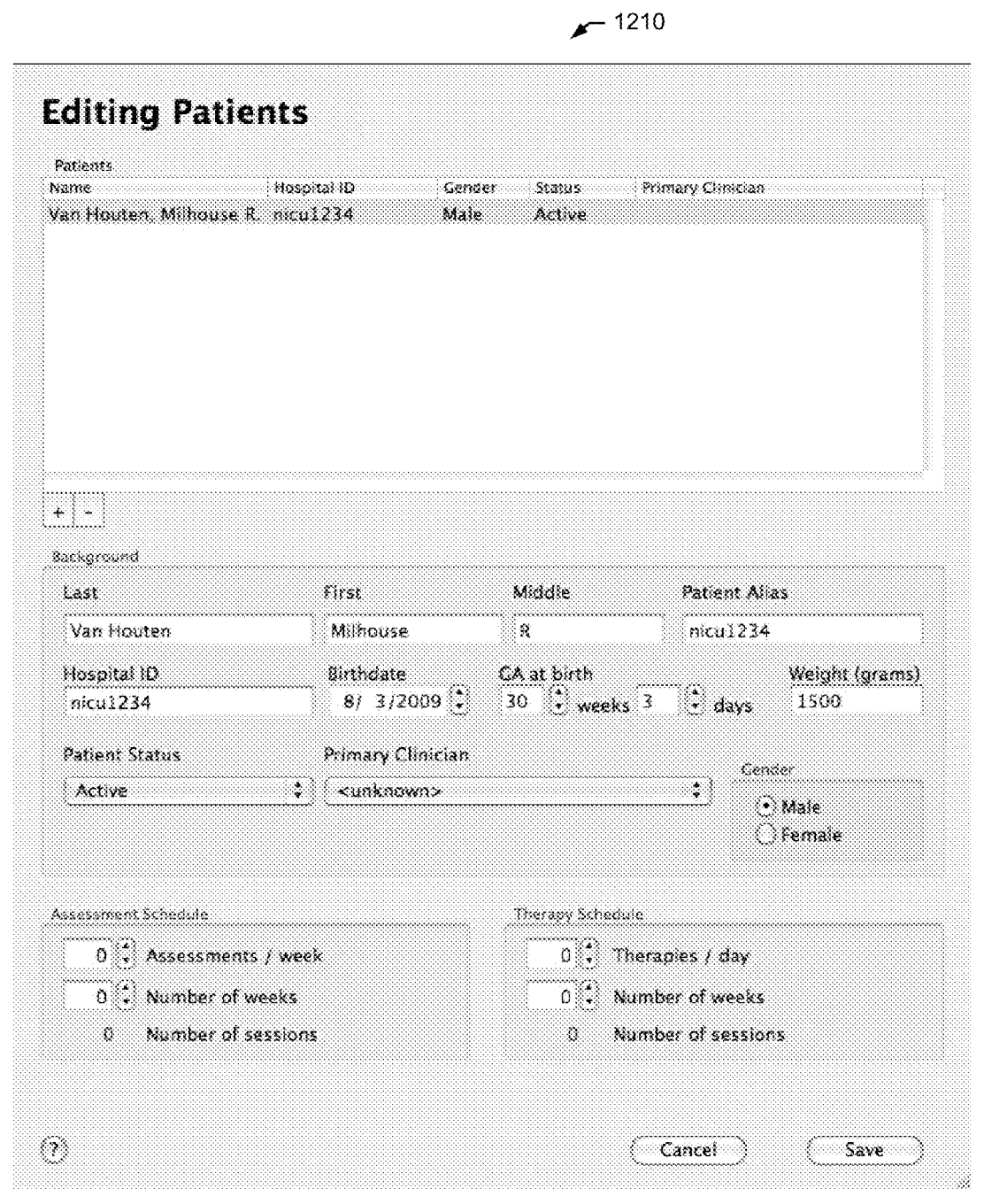

Similarly, the NNS/NS system module 300 includes a patient configuration submodule 404 that allows users of the therapeutic stimulus system 100 with sufficient privileges to add, edit, or delete patients. By way of example and not limitation, an administrator may input data into input forms 1208 and 1210, as shown in FIGS. 16-17, to create, modify, or delete a profile for a patient that may receive an NNS/NS assessment or therapy using the therapeutic stimulus system 100. The NNS/NS system module 300 also includes a session selection submodule 406 that allows users of the therapeutic stimulus system 100 to select whether the NNS/NS system will be used to assess a patient's naturally generated NNS pattern, assess a patient's naturally generated NS pattern and/or to provide therapeutic stimulus to the patient. As such, in response to the type of selection selected by the user, the session selection submodule 406 sends requests to the assessment module 302 and the therapy module 304.

Figure 18:
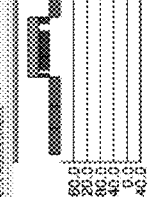
Figure 19:
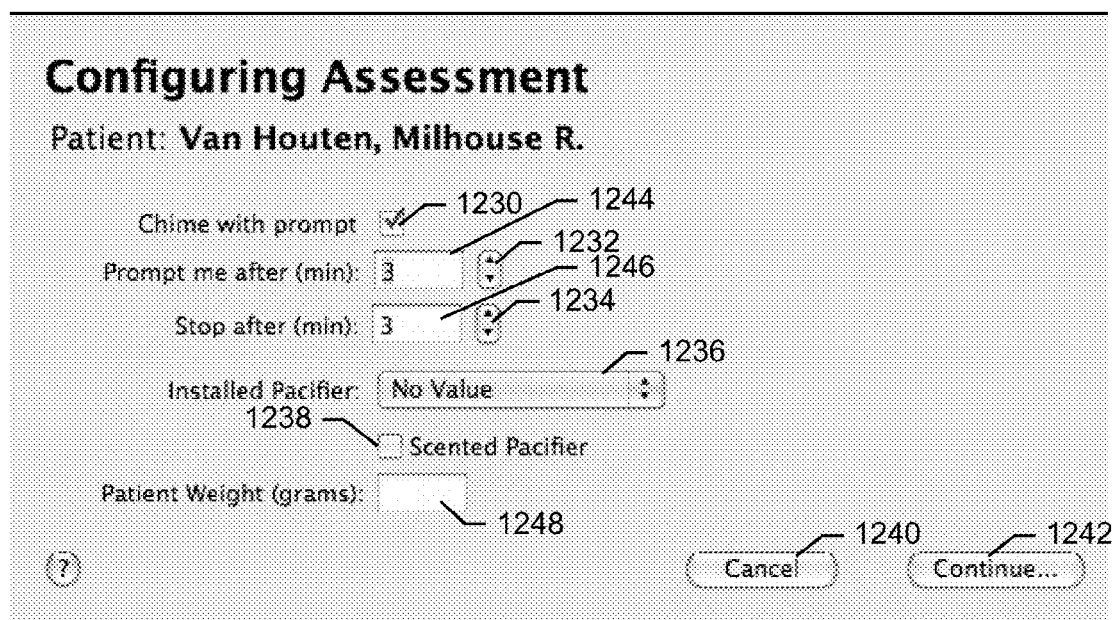
Figure 20:
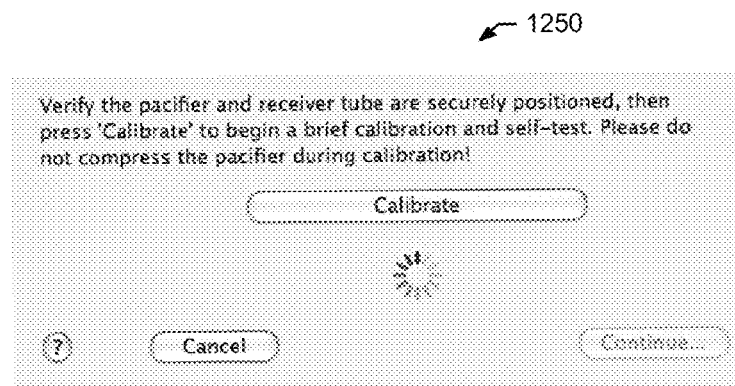
Figure 21:
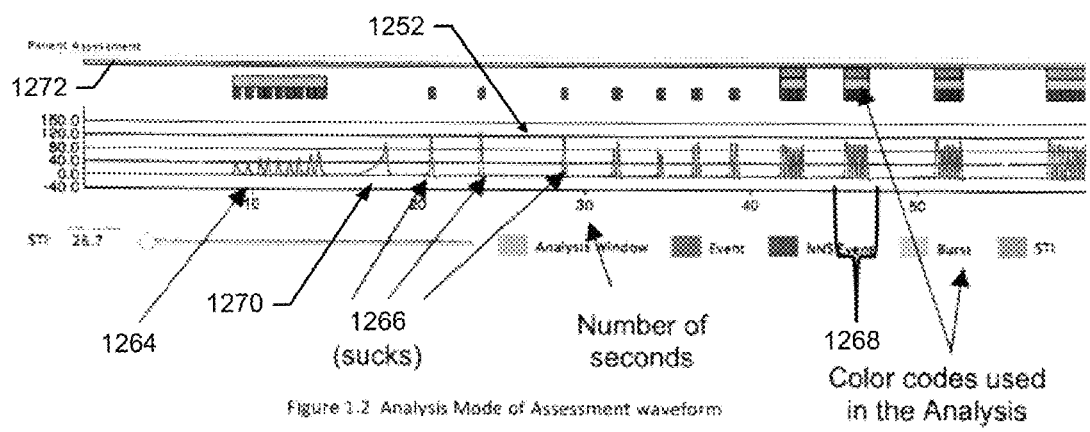
Figure 22:
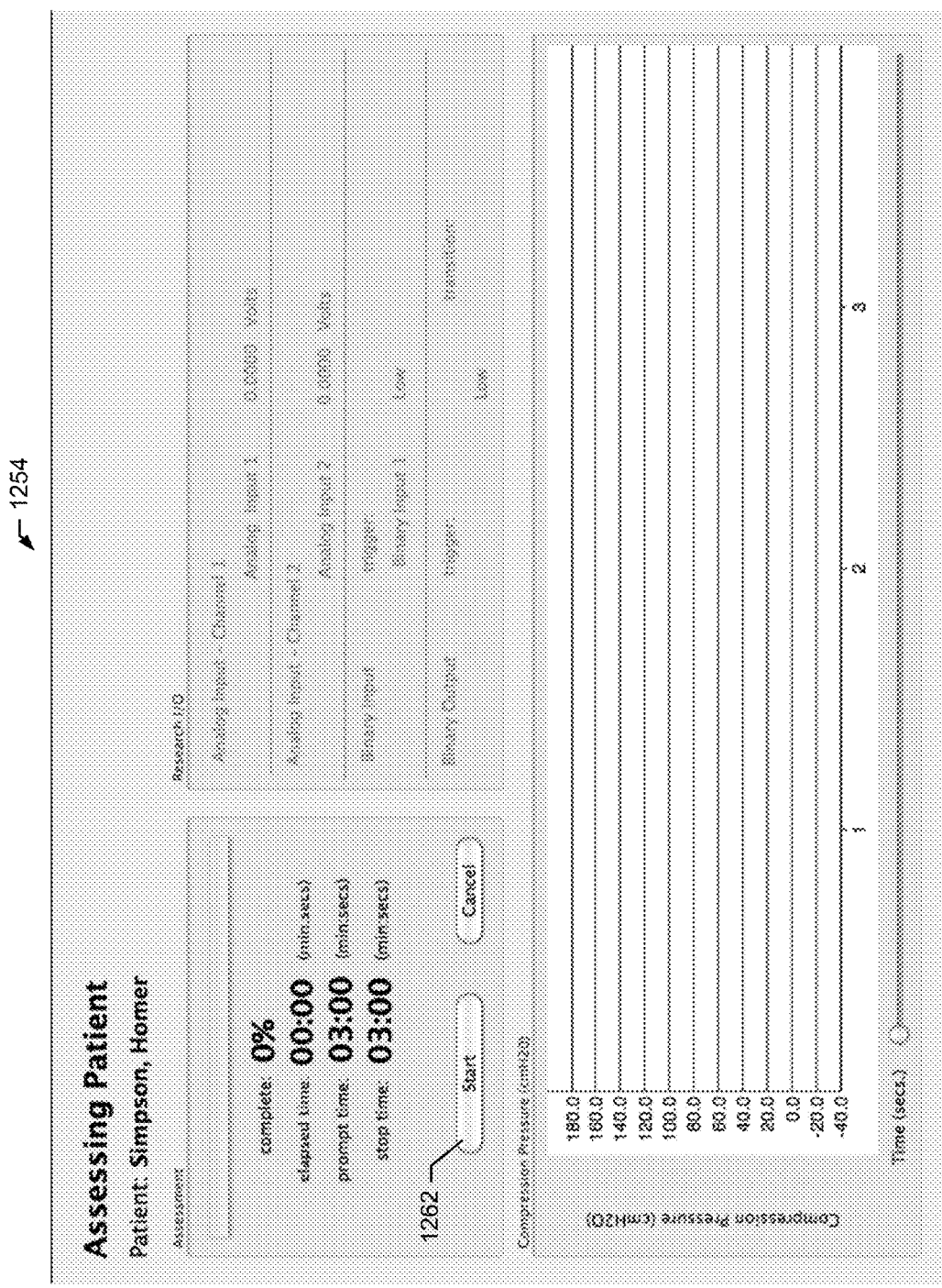
Figure 23:
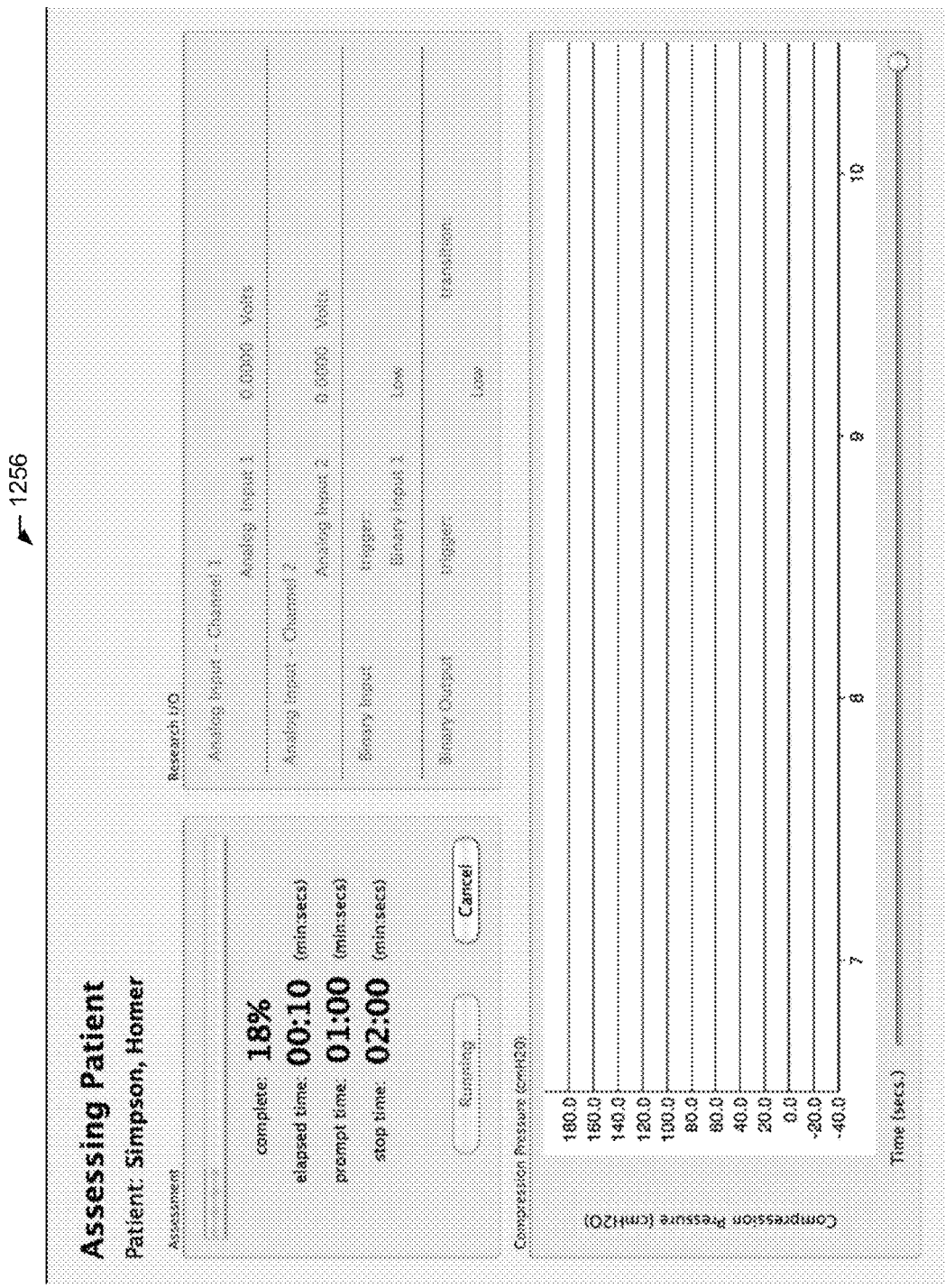
Figure 24:
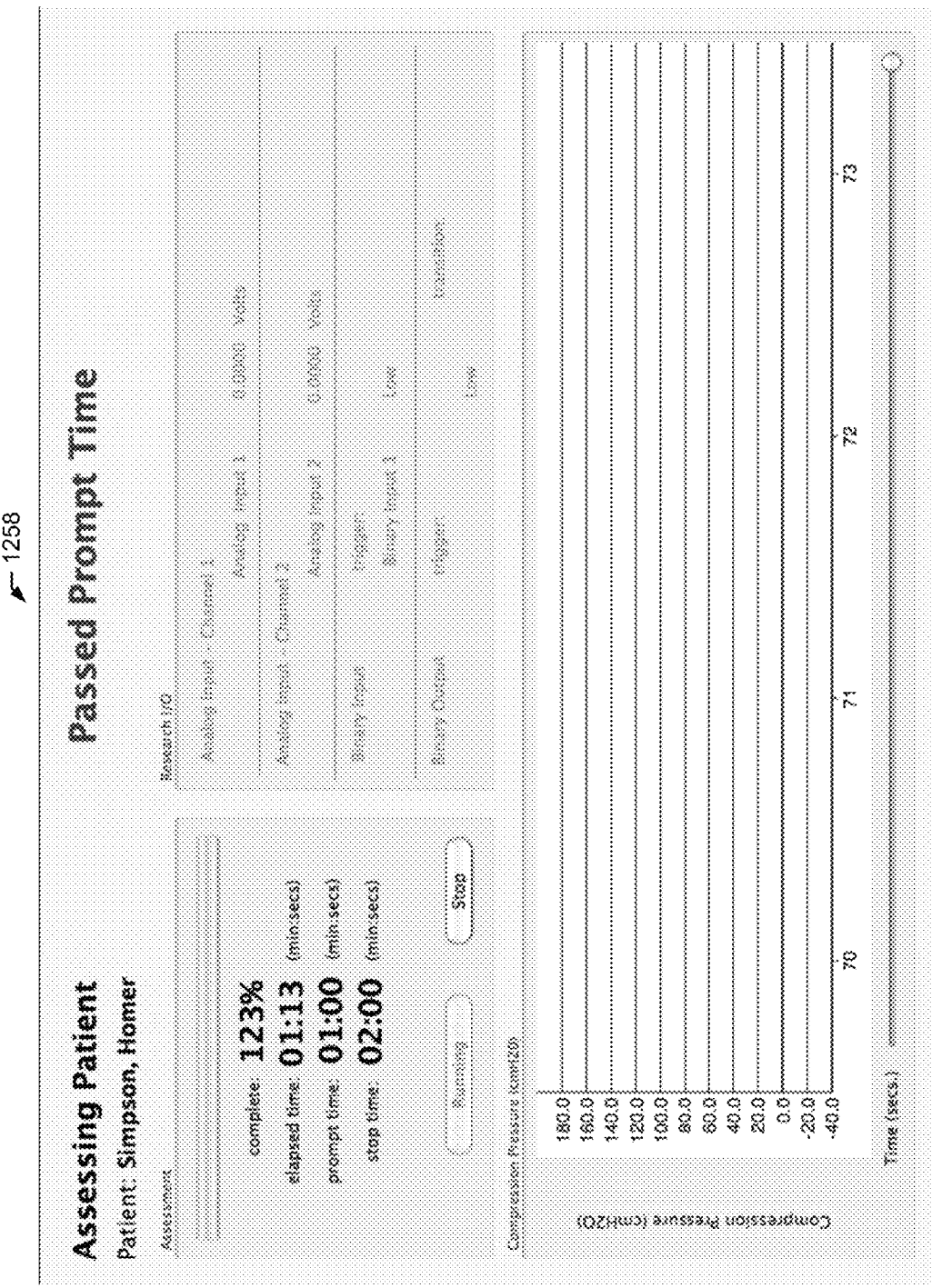
Figure 25:
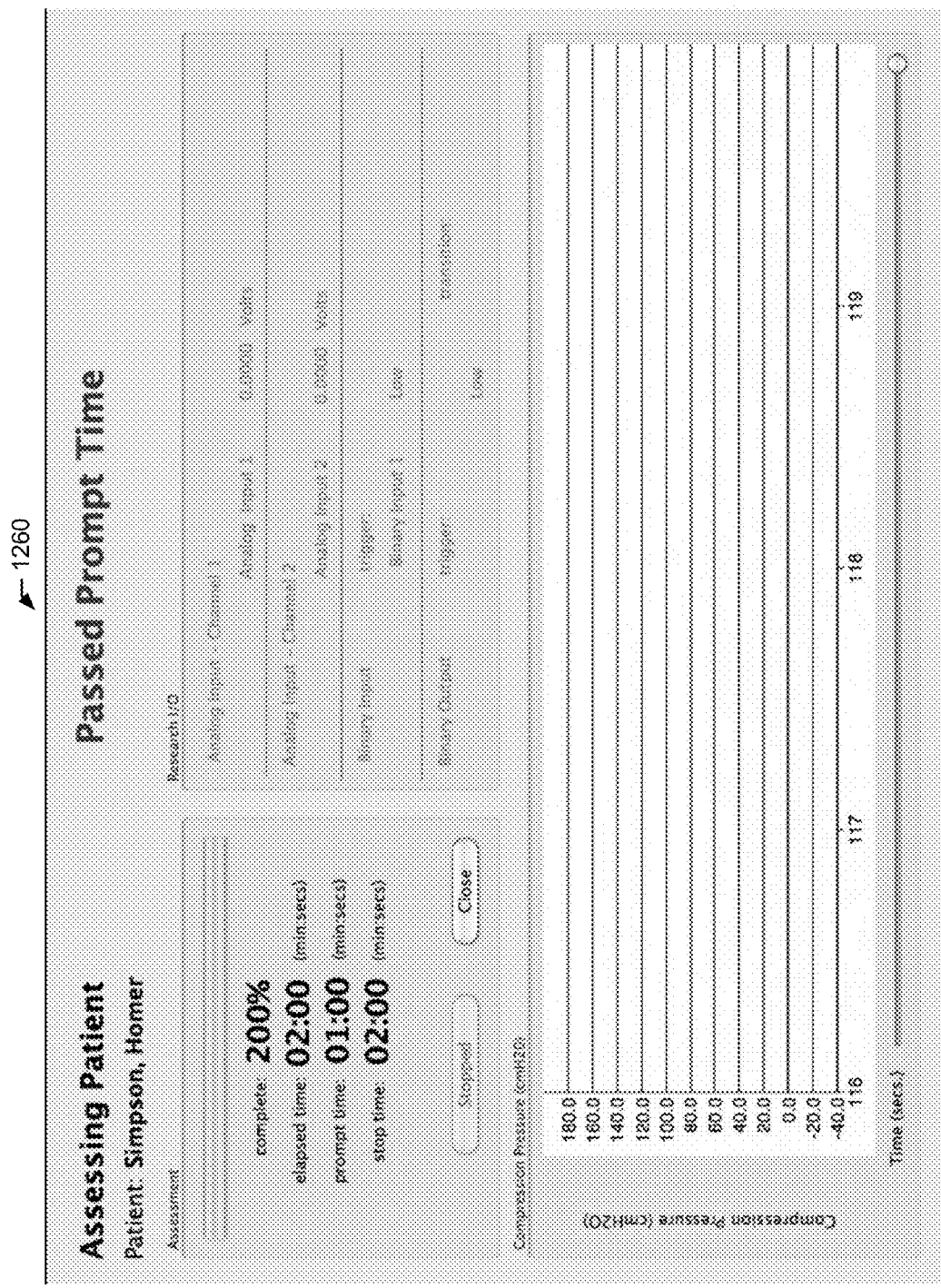
Figure 28:
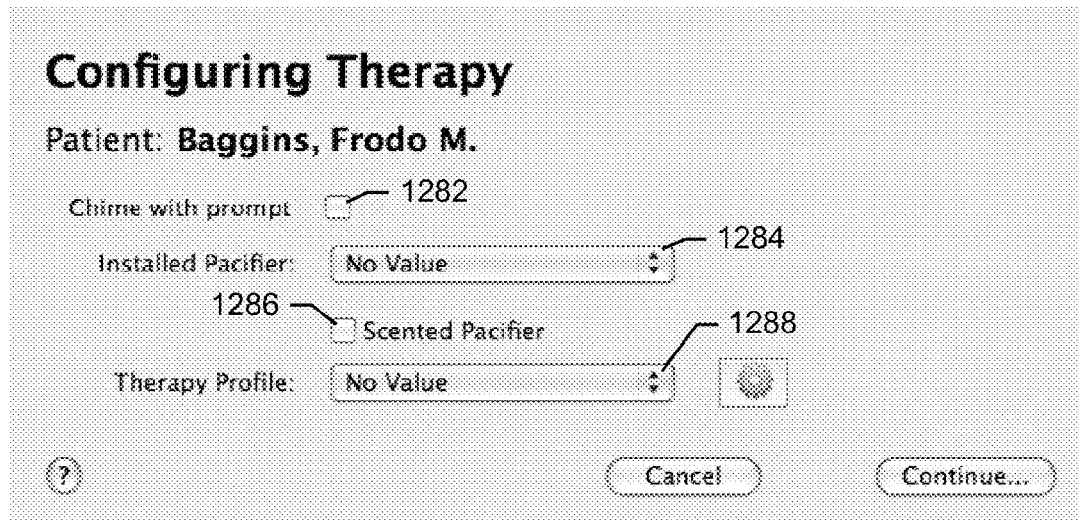

When an assessment request is generated, the NNS/NS system module 300 generates a main assessment input form 1212 to allow the user to input data and interact with the NNS/NS application 204 during the assessment session. By way of example, and not limitation, an embodiment of the main assessment input form 1212 is shown in FIG. 18. In one aspect, the main assessment input form 1212 includes one or more control buttons 1214 to access a list of all the patients actively associated with the NNS/NS application 204. When a patient is selected, the main assessment input form 1212 displays a history 1216 of assessments for the selected patient, and is capable of displaying waveforms from the previous assessments in a waveform frame 1218. In one aspect, the prior waveforms and assessment histories 1216 may be stored as assessment session data 704 in the data source 104.

Figure 31:
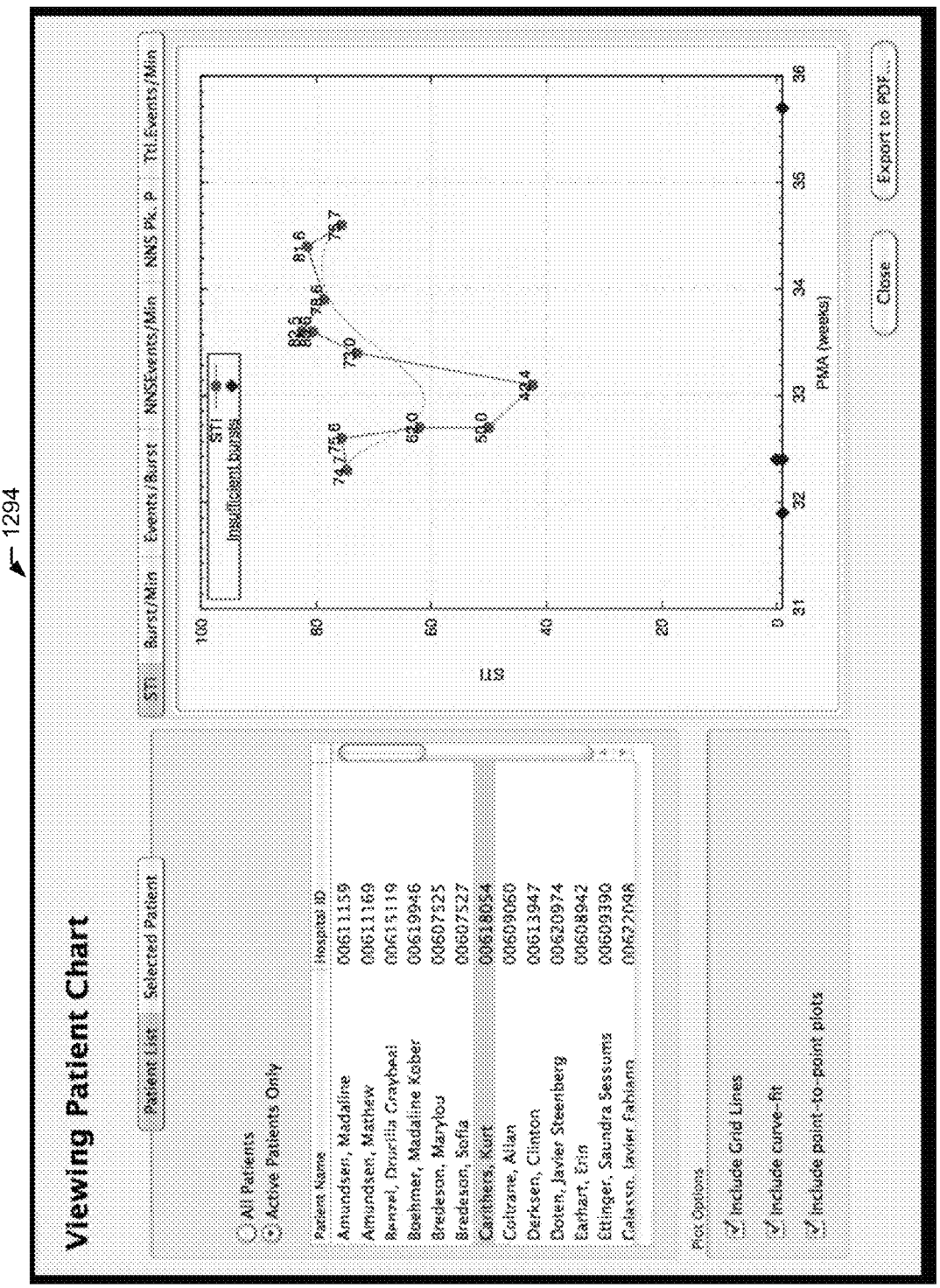

The main assessment input form 1212 also includes a control button 1220 to permit a user to view a patient's medical chart 1294, an example of which is shown in FIG. 31. In addition, the control button 1220 allows the user to add or edit patient data, while control button 1222 allows the user to add notes to the patient assessment data. In addition, the user may select control button 1224 to start a new assessment session for the selected patient or select control button 1226 to switch directly to a therapy session for the selected patient.

In one aspect, the assessment module 302 includes a number of submodules 500-508, including but not limited to an assessment configuration submodule 500, an assessment calibration submodule 502, an assessment capture module 504, a feature extraction submodule 506, and a post-assessment review module 508. The various submodules 500-508 generate and display one or more GUI input forms as shown in FIGS. 19-26 that allow the user to configure, initiate, and review an assessment session.

The assessment configuration submodule 500, for example, generates an assessment configuration GUI input form 1228. The assessment configuration GUI input form 1228 includes one or more controls 1230-1242 and data fields 1244-1248 to input data for selecting or configuring an assessment session. The input data may relate to a total assessment time 1246, an intermediate assessment prompt 1244, a type and configuration 1236 of a baglet or pacifier 810, a type and configuration of a nutritive bottle mechanism 110 and optionally, the patient's weight 1248. As the behavior and mood of a patient is often unpredictable, it is difficult for the user to know in advance how long the assessment session may take. Therefore, the intermediate assessment prompt is selected as a 'best estimate' for the actual time that it may take to capture enough NNS pattern or NS pattern activity to assess the patient. As such, the total assessment time permits the user to continue to collect data, if desired, after the intermediate assessment prompt. In one aspect, the assessment collection submodule 504 halts the capture of assessment data at the intermediate assessment prompt.

The assessment calibration submodule 502 generates an assessment calibration GUI input form 1250. In one aspect, the calibration input form 1250 allows the user to communicate with and configure the pulse generation system 106, the orofacial stimulator appliance 108, and the nutritive bottle mechanism 110 to verify the intended function and calibration for the components of the pulse generation system, the orofacial stimulator appliance, and the nutritive bottle mechanism prior to the initiation of an assessment session.

The assessment capture submodule 504 receives the digital pressure signal from the pulse generation system 106. In one aspect, the assessment capture submodule 504 records and displays the patient's NNS pattern or NS pattern activity as a waveform 1252. In other aspects, the assessment capture submodule 504 may receive and store the digital pressure signal without displaying the NNS pattern activity or NS activity. In another aspect, the assessment capture submodule 504 may display the NNS pattern activity or the NS pattern activity in another form, such as a chart, graph, or table.

The assessment capture submodule 504 may further generate a number of displays during the assessment capture session. For example, FIGS. 22-25 are screen displays that show the progress of the assessment session at the start of the session 1254, at the intermediate prompt interval 1256, at the user input duration time 1258, and at the conclusion of the assessment session 1260. In other aspects, fewer or a greater number of displays 1254-1260 may be provided during the assessment session.

In one aspect, the assessment data capture session may be initiated by input received through a start control button 1262 shown on the display 206. Alternately, the assessment data capture session may be initiated by a switch on a handpiece 806 of the orofacial stimulator appliance 108.

During or subsequent to an assessment session, the feature extraction submodule 506 analyzes the digital pressure signal received by the assessment capture submodule 504. The feature extraction module 506 performs signal processing and feature extraction of a patient's orofacial activity, parameterization of the orofacial activity, and reporting of the activity. In particular, the feature extraction submodule 506 identifies various components of the patient's generated NNS pattern or NS pattern. For example, in the waveform 1252 of FIG. 21, the feature extraction submodule 506 identifies pressure peaks 1264, individual suck events 1266, as well as bursts 1268, which are defined as two or more suck events in less than about 1.2 seconds. In addition, the feature extraction submodule 506 also identifies a number of non-NNS or non-NS events 1270, such as chewing motions made by the patient. The feature extraction submodule 506 also identifies swallowing events and breathing events, among others. In one aspect, the feature extraction submodule 506 may provide annotations, including color-coding, to identify the various NNS events or NS events 1264-1268.

In one aspect, the feature extraction submodule 506 quantifies the overall performance of the patient's generated NNS pattern or NS pattern by assigning a Spatiotemporal Index (STI) value to the pattern. For example, the STI value may be derived by calculating the similarity of up to five individual suck bursts. The STI value measures the symmetrical and repetition of the patient's generated NNS burst pattern or NS burst pattern by integrating the symmetry and quantity of selected NNS events or NS events 1264-1268 in the patient's NNS pattern or NS pattern.

In another aspect, the feature extraction submodule 506 automatically determines a number of parameters that are desirable for evaluating the patient's generated NNS pattern or NS pattern and determining the best course of therapy to treat the patient. For example, the evaluation parameters may include the STI value for the waveform, the number of bursts per minute, the number of events per burst, the number of NNS events or NS events per minute, an average peak pressure, as well as the total number of events per minute. In other examples, a fewer or greater number of parameters as well as different parameters may be considered when evaluating the patient's generated NNS pattern or the patient's generated NS pattern.

The evaluation parameters may be determined using a portion or subset of the collected assessment data. For example, a "most active" two-minute window having the most number of NNS events or NS events is identified by the feature extraction submodule 506. The most-active window is generally indicated by a bar 1272 on the displayed waveform 1252. When calculating the six evaluation parameters, the feature extraction submodule 506 may ignore any NNS/NS activity outside of the most-active window.

In another aspect, the feature extraction submodule 506 conducts predictive assessment. The predictive assessment may reveal one or more deficiencies of primary suck characteristics that are neurologically controlled. The deficiencies may relate to the regularity and number of individual sucks in individual NNS bursts, the organization of collective suck bursts such that stimulation may be needed to increase a level of central suck pattern generator development, the intensity of effort such that NNS practice or therapy may be needed to gain muscle strength or endurance, or the absence of NNS activity (e.g., immature suck function).

After capturing the patient's generated NNS pattern or NS pattern and determining the evaluation parameters, the post assessment review module 508 generates a post-session GUI input form 1274 where the user may confirm the identity of the patient that underwent the assessment session and input notes regarding the assessment session. By way of example and not limitation, the user may indicate the state of alertness for the patient, by inputting terms such as alert, crying, drowsy, sleepy, or any other term that identifies the patient's level of alertness during the assessment session. The user may further quantify the patient's state of alertness as active or quiet, as the patient's STI value may fluctuate between assessment sessions due to the patient drifting off to sleep during the capture period.

Additionally, the post assessment review module 508 may provide feedback indicating predictions of one or more areas of neurological muscle activity that may need further development. In an embodiment, the post assessment review module 508 may provide information and output regarding the one or more deficiencies of the primary suck characteristics that are neurologically controlled. As an example, if during the assessment the patient demonstrates a weak NNS average suck pressure (e.g., least than or equal to ten $cmH_2O$), this may suggest that musculature of the patient requires practice to develop endurance and compressive force. The post assessment review module 508 may recommend that a patient develop strength through therapy with a pacifier, physical stimulation, or by repeated therapy with the therapeutic stimulus system 100 whereby NNS of the patient is stimulated by the therapy pulse. NNS suck pressure in and/or around a range of fifteen-twenty $cmH_2O$ and/or twenty or more NNS suck bursts per minute may indicate that the patient has progressed and may be ready to initiate oral feeding.

Once a patient has been diagnosed or characterized as having a disorganized NNS pattern or disorganized NS pattern, it is often desirable for the patient to undergo a therapy session to entrain the patient's sCPG to produce an organized NNS pattern and/or NS pattern. Typically, a therapy session consists of applying an external stimulus to or near the lips and mouth of the patient in order to modify the NNS pattern generated by the sCPG. As another example, a therapy session includes applying the external stimulus and moderates the stimulus based on patient performance. A therapy session may also include introduction of the nutritive bottle mechanism 110 that provides a nutritive bolus. The nutritive bolus may have a fixed volume or may have a volume that is defined by a pressure and nutritive suck of a patient, such that the patient must exert a greater effort to increase a volume of the bolus.

Figure 9:
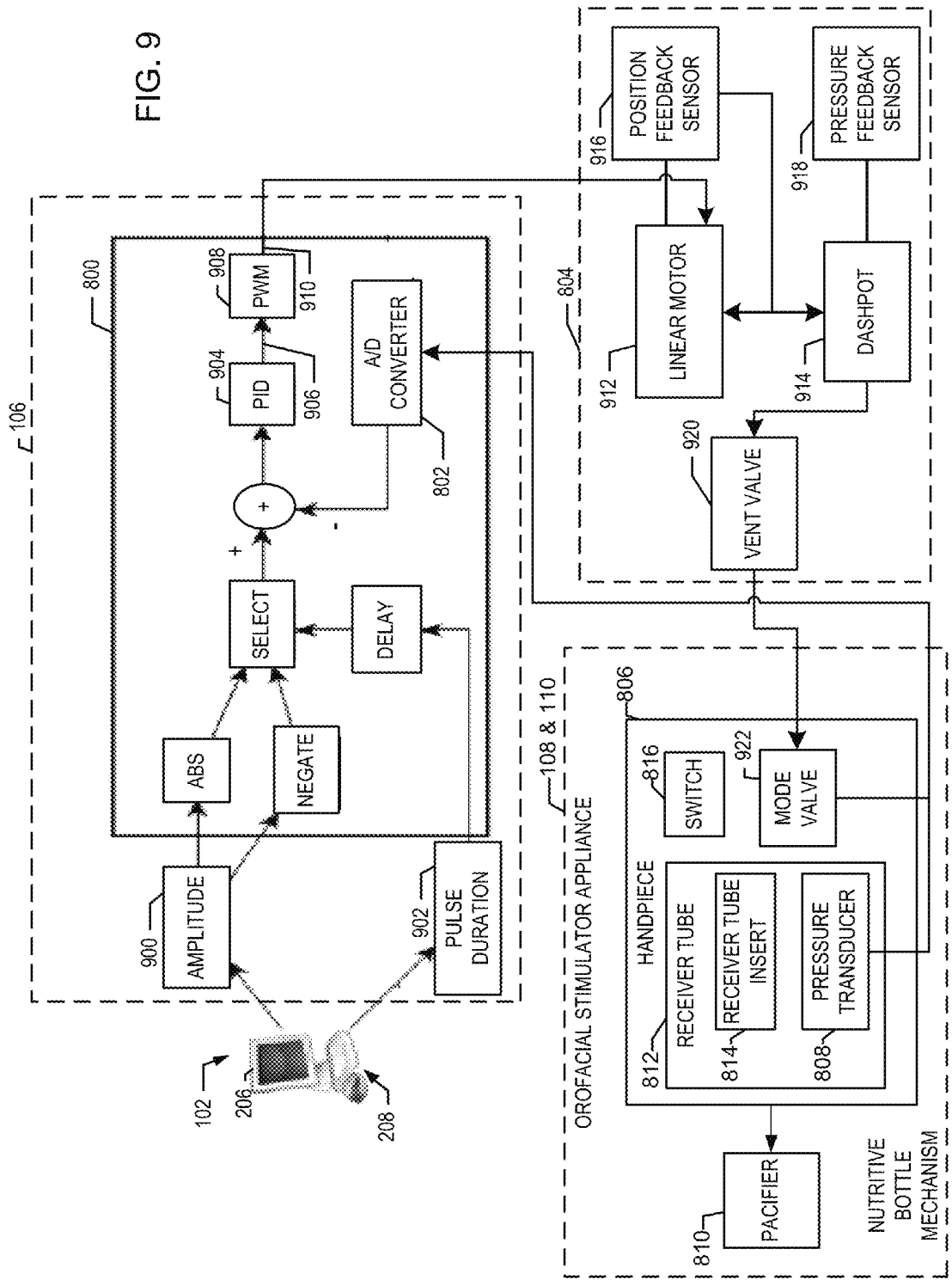
FIG. 9 is a block diagram of a therapeutic stimulus system according to one aspect.

The orofacial stimulator appliance 108 contacts the patient on or near the lips and mouth to deliver therapeutic stimulation, provided by the pacifier's motion as caused by the pressure pulses, to the patient's orofacial nerves via regulated changes in the surface diameter of a pacifier 810 that is a component of the orofacial stimulator appliance 108, as shown in FIGS. 8B and 9. The pressure pulses conveyed by the orofacial stimulator appliance 108 are actuated at the pulse generator or pulse transducer system 104 in response to a therapy pulse profile generated by the therapy module 304.

Figure 27:
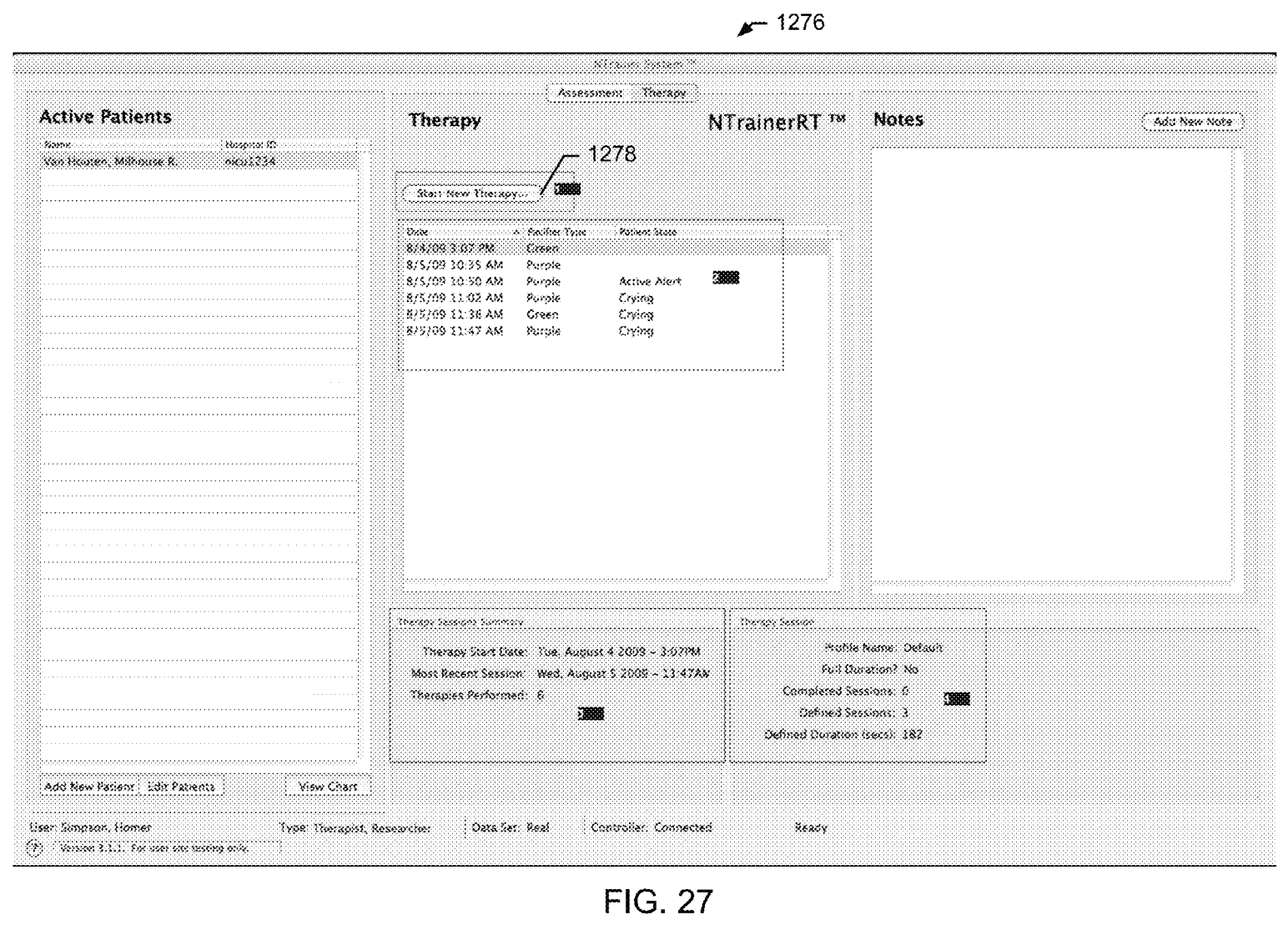

When a therapy session is to be performed, the NNS/NS system module 300 generates a main therapy GUI input form 1276, as shown in FIG. 27. The main therapy GUI input form 1276 includes a control button 1278 to allow a user to start a new therapy session. The main therapy GUI input form 1276 also includes a control button to display previous therapy session data 706 stored in the data source 104, and the therapy session data 706 includes summaries and detailed information for previous therapy sessions.

In one aspect, the therapy module 304 communicates with the real-time application 209 and includes a number of submodules 600-606, including but not limited to a therapy configuration submodule 600, a therapy calibration submodule 602, a therapy execution submodule 604, and a post-therapy review submodule 606. The various submodules 600-606 generate one or more GUI input forms for display that allow the user to configure, execute, and review a therapy session.

The therapy configuration submodule 600, for example, generates a therapy configuration input form 1280. The assessment configuration GUI input form 1280 includes a number of controls 1282-1286 related to the therapy session, the pacifier 810 of the orofacial stimulator appliance 108, and the nutritive bottle mechanism 110. The assessment configuration GUI input form 1280 also includes a control button 1288 that allows the user to select or modify one or more therapy pulse profiles.

A therapy pulse profile consists of one or more therapeutic waveforms that result in variable but controlled radial displacements of the outer surface of the pacifier 810. The surface displacements of the pacifier 810 provide a tactile stimulus to or near the lips and mouth (e.g., intraoral, anterior tongue tip, anterior tongue dorsum) of the patient to entrain the patient's sCPG to naturally produce a NNS/NS pattern that mimics the generated therapy waveforms. Once configured, the therapy waveforms are actuated by the pulse generation system 106, as shown in FIGS. 8A and 9.

The therapy calibration submodule 604 functions similar to the assessment calibration submodule 502 and generates a therapy calibration GUI input form similar to the assessment calibration GUI input form 1250. In one aspect, the calibration GUI input form allows the user to communicate with and configure the pulse generation system 106, the orofacial stimulator appliance 108, and the nutritive bottle mechanism 110 to verify the intended function and calibration of the instruments prior to the start of the therapy session.

The therapy execution submodule 604 captures and displays the patient's NNS/NS pattern activity during a therapy session. Additionally, if applicable, the therapy execution submodule 604 provides reactive pulse training via the orofacial stimulator appliance 108, nutritive, reactive therapy via the nutritive bottle mechanism 110, and/or nutritive, reactive, and adaptive therapy via the nutritive bottle mechanism.

Figure 29:
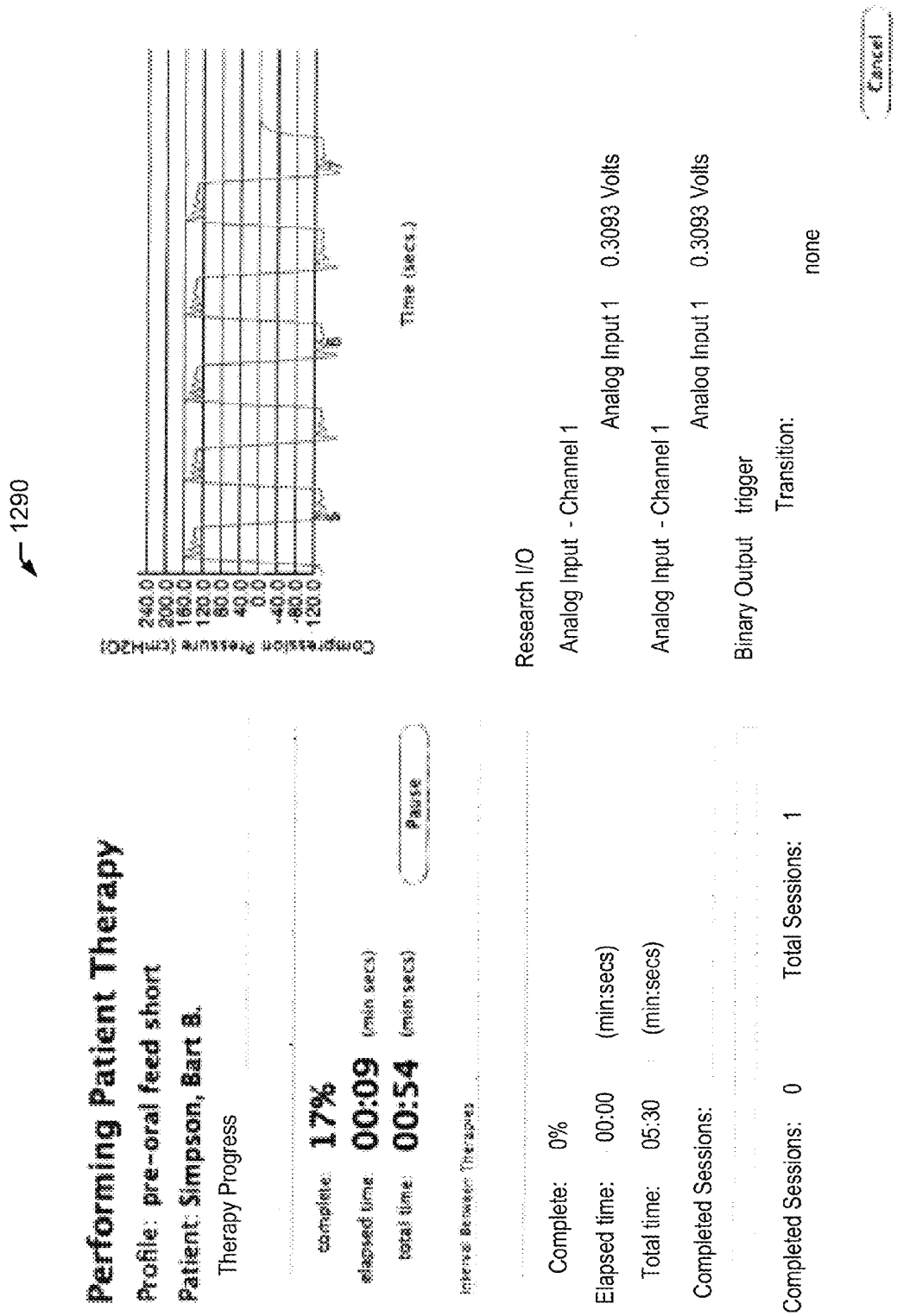

The therapy execution submodule 604 may generate a display 1290, as shown in FIG. 29, that shows progress of the therapy session at the start of the session, during the therapy session, at a rest interval, and at the conclusion of the therapy session, respectively. In other aspects, fewer or a greater number of displays may be provided during the therapy session.

Similar to an assessment session, the therapy session may be initiated by input received through the start control button 1278 of the GUI input form 1276. Alternately, the therapy session may be initiated by a switch 816 on a handpiece 806 of the orofacial stimulator appliance 108. The switch 816 may be any suitable switch including, but not limited to a push-button switch or a toggle switch. Further, the switch 816 may be used to alternate between a therapy mode and an assessment mode and/or to activate the therapy mode or assessment mode.

After a therapy session, the post-therapy review submodule 606 generates a post-session GUI input form similar to the assessment post session GUI input form 1274 where the user inputs notes regarding the therapy session. The user may indicate the state of alertness for the patient, such as alert, crying, drowsy, or sleepy.

The NNS/NS application 204 further includes a leak detection module 306. The leak detection module 306 continuously monitors the performance of pneumatic subsystems within the pulse generator system 104, the pneumatic lines and connections of the orofacial stimulator appliance 108 to detect air leaks, and the nutritive bottle mechanism 110.

Figure 30:
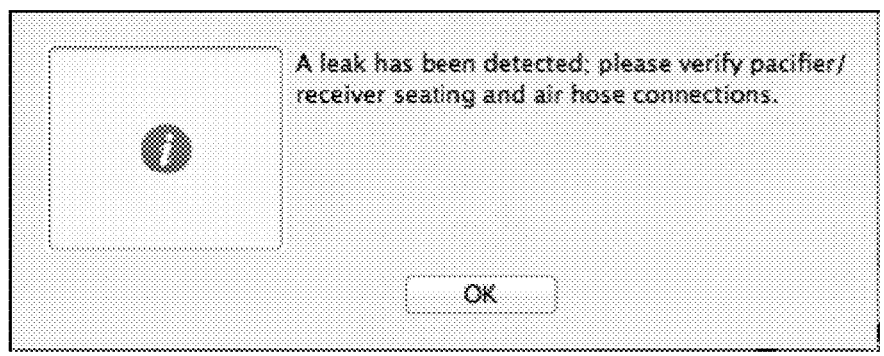

In one aspect, the leak detection module 306 determines that there may be an air leak by identifying reduced pulse amplitudes, increased pulse roll-offs, and/or the need for a greater stroke length in the pneumatic pulse generator 804 to generate the requested pressure. Further, the leak detection module 306 can identify air leaks caused by disconnected airlines, and poorly seated receiver tubes or pacifiers. The module 306 will display a warning 1292, as shown in FIG. 30, requiring the user to address the leak. The leak detection module 306 may monitor the therapeutic stimulus system 100 automatically and continuously during both assessment and therapy sessions.

The NNS/NS application 204 also includes the research module 308 that allows a user of therapeutic stimulus system 100 to conduct various research experiments and protocols. In particular, the research module 308 receives and transmits data to an input/output (I/O) port of the computing device 102 or the real-time controller 800 of the pulse generation system 106. The I/O port, in turn, may be in communication with any of a variety of external instruments for conducting research.

In various other aspects, the NNS/NS application 204 may include additional modules for other functions, including those typically associated with medical or rehabilitation facilities. By way of example and not limitation, the NNS/NS application 204 may also include a billing module to interface with an existing billing system or a printing module for printing various data, charts, or reports.

The NNS/NS Therapeutic Appliance Assembly

Referring now to FIGS. 1, 8A-B, and 9, the NNS/NS Therapeutic appliance assembly includes the pulse generation system 106, the orofacial stimulator appliance 108, and the nutritive bottle mechanism 110.

During an assessment session, the computing device 102 may record and display a signal received from a pressure transducer 808 of the orofacial stimulator appliance 108, as shown in FIG. 8B as well as record and display a signal received from the transducer 808 connected to the nutritive bottle mechanism 110. The transducer 808 translates pressure changes caused by sucking and mouthing movements of the patient into an analog signal that tracks the pressure applied to a pacifier 810 versus time. The transducer 808 detects a swallowing action of the patient and translates the swallowing action into an analog signal that tracks the swallowing versus time. The transducer 808 determines a negative oral cavity pressure and a compression force of the pacifier 810 by the patient. Determination of the negative oral cavity pressure and the compression force provides additional diagnostic information associated with the patient and furthers NNS/NS development. In one aspect, NNS is a compressive activity associated primarily with movement of the jaw and tongue in a patient. As the patient's suck function develops, the ability to generate a negative oral cavity pressure aids in the feeding success for both nipple and bottle feeding.

The analog pressure signals are converted to a digital signal at an analog-to-digital convertor 802 of the pulse generation system 106, as shown in FIG. 8A. The analogto-digital converter 802 is incorporated into a real-time controller 800, that receives and modifies received and/or generated pressure signals in real-time. The digital pressure signal is then received, recorded, and displayed by the assessment module 302.

Similarly, in one aspect of a therapy session, the pulse generation system 106 receives amplitude data 900 and pulse duration data 902 for the desired waveforms. The amplitude data 900 and the pulse duration data are provided to the real-time controller 800 which may include an H-bridge (not shown) and a proportional—integral—derivative controller (PID controller) 904. By way of example and not limitation, the PID controller 904 may be a CompactRIO controller. The PID controller 904 generates a signal 906 that is fed through a pulse-width modulation (PWM) component 908. The modulated signal 910 is then provided to a motor 912 of the pneumatic pulse generator 804. In one embodiment, the pneumatic pulse generator 804 consists of a linear motor 912 mechanically engaged to an air cylinder, such as but not limited to an Airpel airpot or other device having a piston fitted in a precision bore cylinder with position and pressure feedback sensors in communication with the PID controller 904. The pulse generator 804 also includes a position feedback sensor 916 to monitor the position of the piston of the dashpot 914 and a pressure feedback sensor 918 to monitor the pressure with the dashpot 914. The air displaced by the pneumatic pulse generator 804 is then transmitted to the handpiece 806, through one or more pneumatic airlines, where the therapy waveform displaces the outer surface of the pacifier 810. The pulse generator 804 may also include a vent valve 920 that is normally closed, however the valve may be opened and vented to atmosphere to ensure pressure equilibrium at the start of each assessment or therapy session. Optionally, the pulse generator 804 may also include another valve (not shown) that isolates the dashpot 914 from the handpiece 806 during a Power-On Self Test (POST). The optional valve therefore permits diagnostic testing of the therapeutic stimulus system 100.

The orofacial stimulator appliance 108 includes the handpiece 806 and the pacifier 810 that are brought into contact with the patient to deliver the therapeutic stimuli. In one aspect, the handpiece 806 includes a receiver tube 812 in fluid communication with the interior of the baglet or pacifier 810. The receiver tube 812 includes an interior void for receiving a volume of air from the pneumatic pulse generator 804 or from the pacifier 810. Optionally, the handpiece 806 also includes a receiver tube insert 814, that may be inserted in to the receiver tube 812 to limit the total volume of air in the interior void of receiver tube. The handpiece 806 may also include a mode valve 922 that is opened or closed depending on whether an assessment session or a therapy session is to be performed.

In other aspects, the orofacial stimulator appliance 108 may include a piezoelectric system for generating an electrical charge in response to a mechanical stress or generating a mechanical stress in response to an electrical charge. Further, the orofacial stimulator appliance 108 may produce or at least project sound waves to deliver the therapeutic stimuli. For example, the orofacial stimulator appliance 108 may include a speaker or other electroacoustic transducer (not shown) to project sonic waves that stimulate the patient. The signals 906 and 910 or a signal to generate the sonic wave may be high-velocity signals. Preferably, the stimulus provided by the displacement of the outer surface of the pacifier 810 is recognized above and beyond any background activity or noise of the patient or the therapeutic stimulus system 100.

In one aspect, the expansion characteristics of the therapy pulses as delivered by expansion of the pacifier are verified using a laser micrometer (not shown). The data from the laser micrometer regarding the frequency and amplitude components of the therapy pulse at the pacifier 810 may be digitized, recorded, and analyzed by the NNS/NS application 204.

Preferably, the pacifier 810 is a Soothie NICU® pacifier or a Wee Soothie® pacifier; however, the size, shape, and/or type of pacifier 810 may vary between procedures and/or patients. In addition, one or all of the pulse generation system 106, the orofacial stimulator appliance 108, and the nutritive bottle mechanism 110 may be configured for each particular patient.

Figure 33:
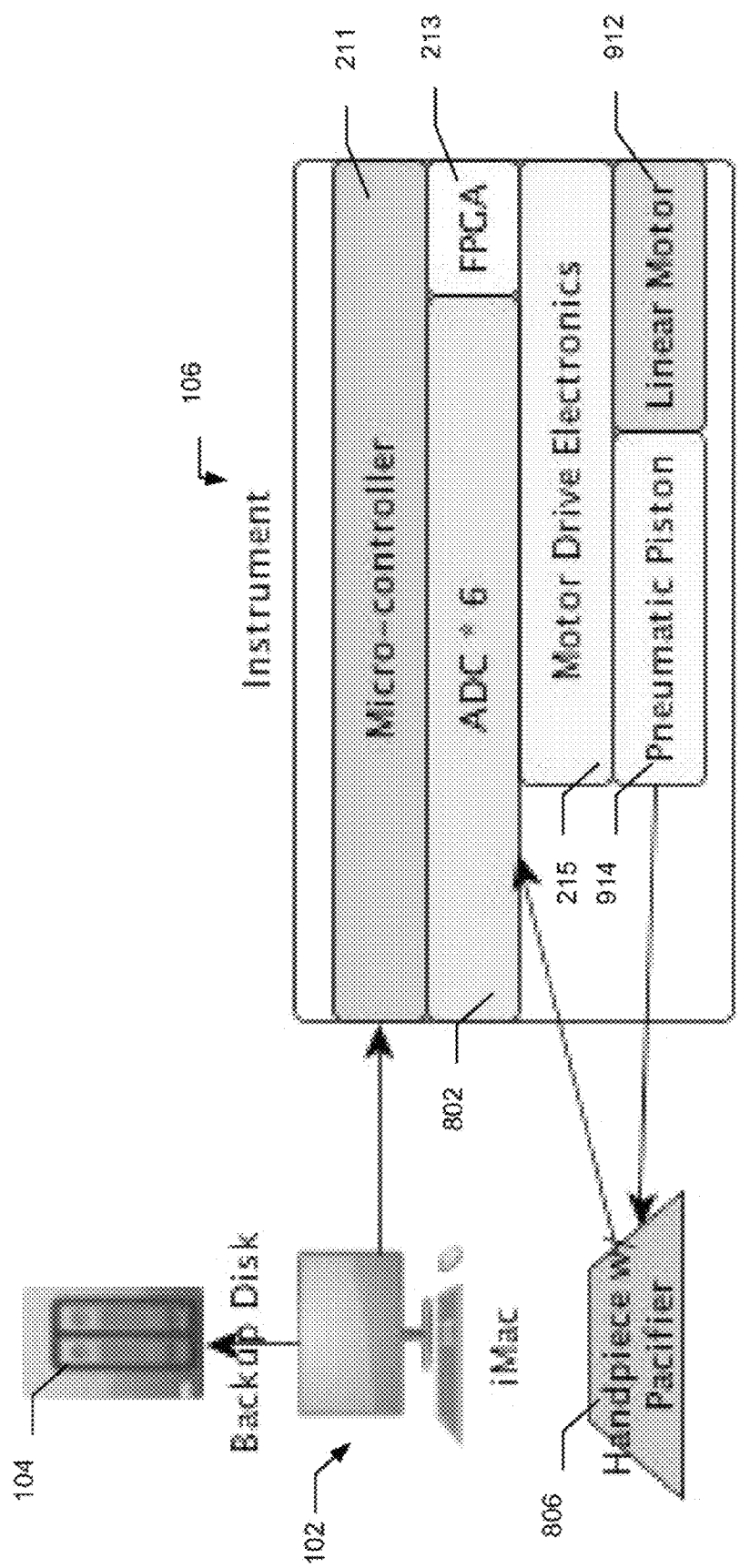
FIG. 33 is an illustration of an assessment device used in system to predict and improve a patient oral feeding ability according to one aspect.

FIGS. 32 and 33 are block diagrams of additional embodiments of the therapeutic stimulus system 100. In particular, one embodiment of the stimulus system 100 includes the NNS/NS application 204, executed on the computing device 102 that is associated with a variety of devices to assess the feeding capabilities of a patient. The patient may be a neonate, an infant who was born prematurely, a patient with congenital heart defects, or any other patient with undeveloped and/or under-development motor skills for oral feeding, regardless of age.

Similar to other embodiments, the application 204 generates one or more user interfaces 205, which may include those shown in FIGS. 12-31. The application 204 also includes an assessment module or controller 302 and a therapy module or controller 304. In one aspect, the application 204 also includes an instrument driver 207, that may be code, other software or a hardware device, that communicates with another instance of the application or another real-time assessment application 209, executing on an assessment device, such as an embodiment of the pulse generation system 106, shown in FIG. 33.

In one aspect, the assessment module 302 includes sub-modules 500-508 that perform signal processing and feature extraction of a patient orofacial activity, parameterization of the orofacial activity, patient nutritive bottle activity, parameterization of the bottle activity, and reporting of the activity to the user, a display device of the computing device 102, or to the data storage 104. The orofacial activity and the bottle activity may also be shared with a patient management module 404 that also communicates with the data storage 104.

The assessment device or pulse generation system 106, as shown in FIG. 32, includes a micro-controller or processor 211, which may be the controller 800 as shown in FIG. 8A, an analog-to-digital convertor 802, a field-programmable gate array (FPGA) 213, various motor drive electronics 215, a pneumatic piston, such as the dashpot 914 shown in FIG. 9, a motor 912, and a hand piece 806. The hand piece 806 may also include the pacifier 810 that is contacted with the patient. In one aspect, the assessment device 106 is in communication with the computing device 102.

The Therapeutic Waveform

Figure 10A:
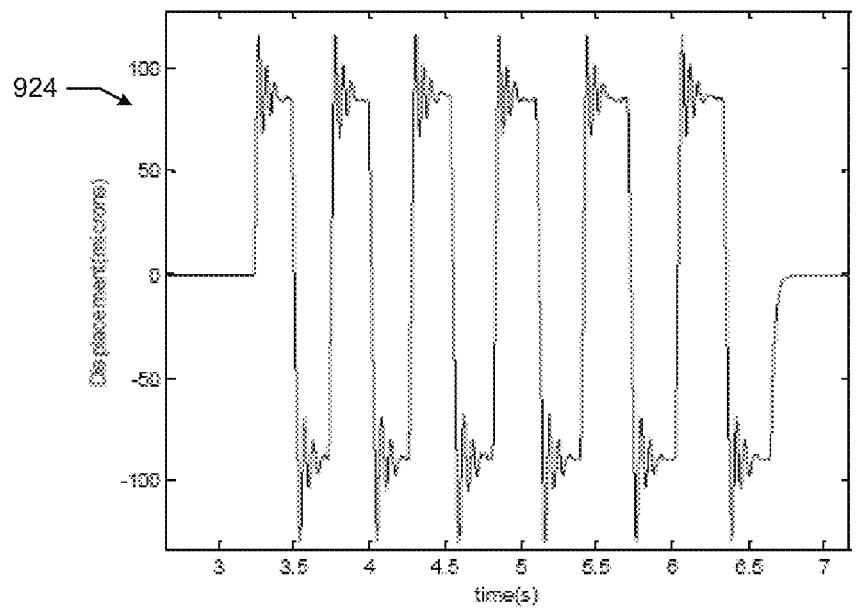
FIG. 10A is a graph depicting the displacement of pacifier in response to a therapeutic pressure pulse sequence according to one aspect.
Figure 10B:
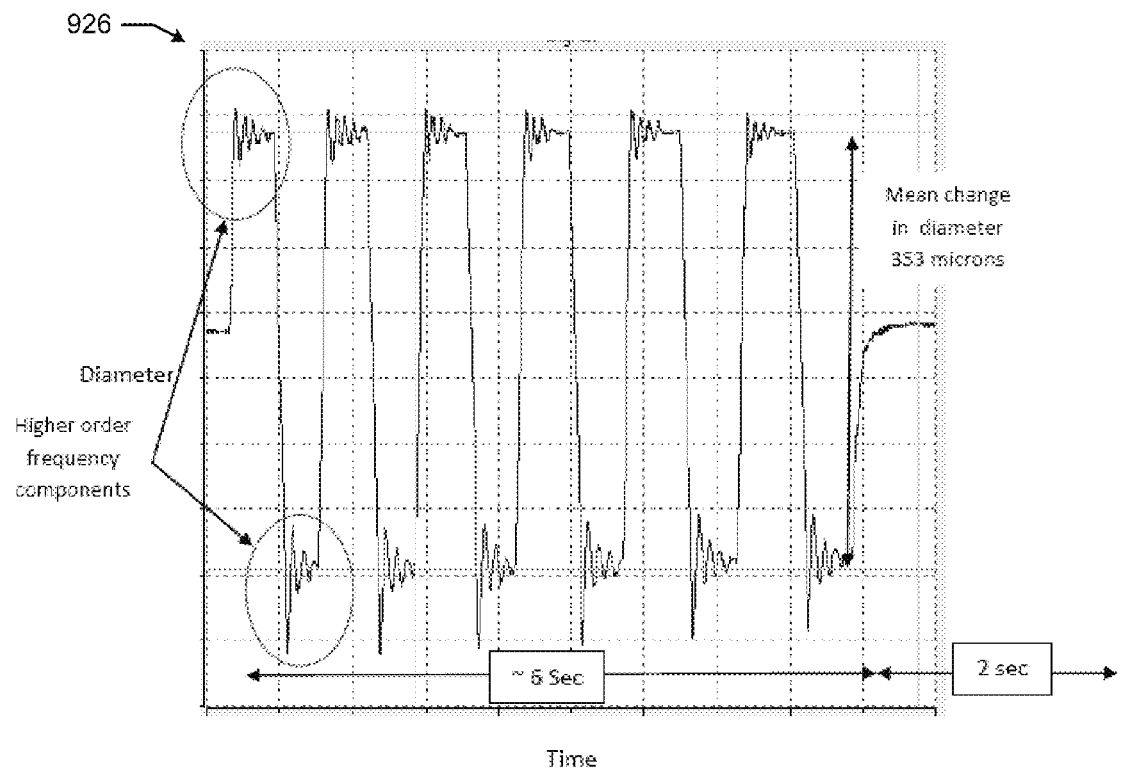
FIG. 10B is a graph depicting the change in the mean diameter of a pacifier in response to a pressure pulse according to one aspect.

Preferably, the therapy waveform consists of one or more salient therapeutic bursts and each burst contains two or more square wave pulses. Typically, the bursts are separated by a configurable and variable delay interval. FIGS. 10A and 10B depict plots 924 and 926 that indicate changes in the pacifier 810 in response to a sequence of the therapy waveforms.

According to one aspect, the nominal number of pulses in a desired therapeutic burst is six, while the actual number is configurable by users of the therapeutic stimulus system 100. Preferably, each pulse in a therapeutic burst is a square wave pulse having the same configurable amplitude. Further, the period of each pulse increases sequentially thereby, causing the waveform frequency to slow down from the start of the therapeutic burst to the end of the therapeutic burst. A desirable decelerating sequence pulse sequence has periods of approximately $510\pm3$ ms, $526\pm3$ ms, $551\pm3$ ms, $580\pm3$ ms, and $626\pm3$ ms between therapeutic bursts. When more than five pulses are used in the therapeutic burst, the sixth and all subsequent pulses have an periodic interval of approximately 626 ms.

Figure 10C:
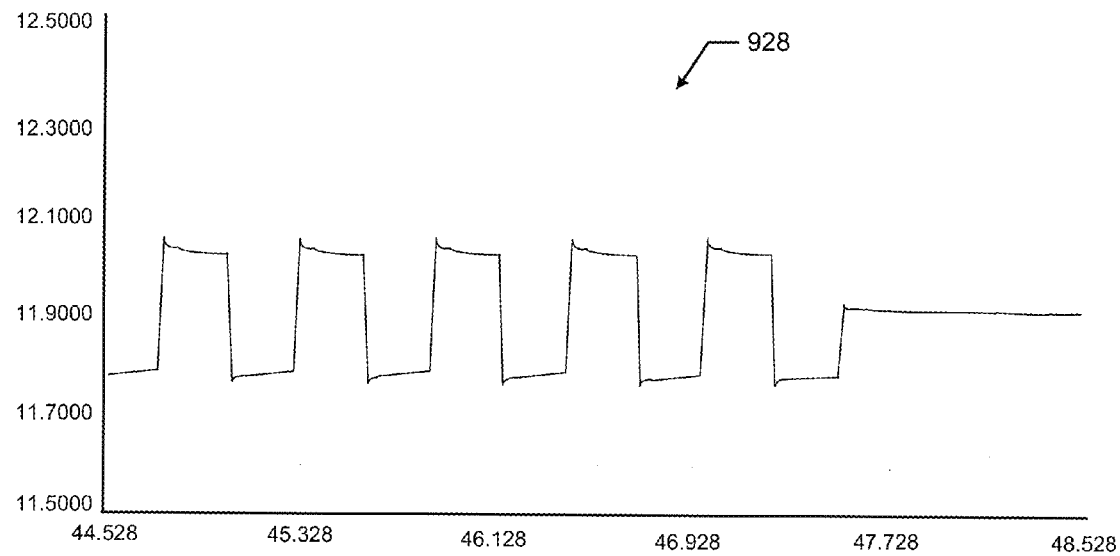
FIG. 10C is a graph depicting a therapeutic burst according to one aspect.
Figure 10D:
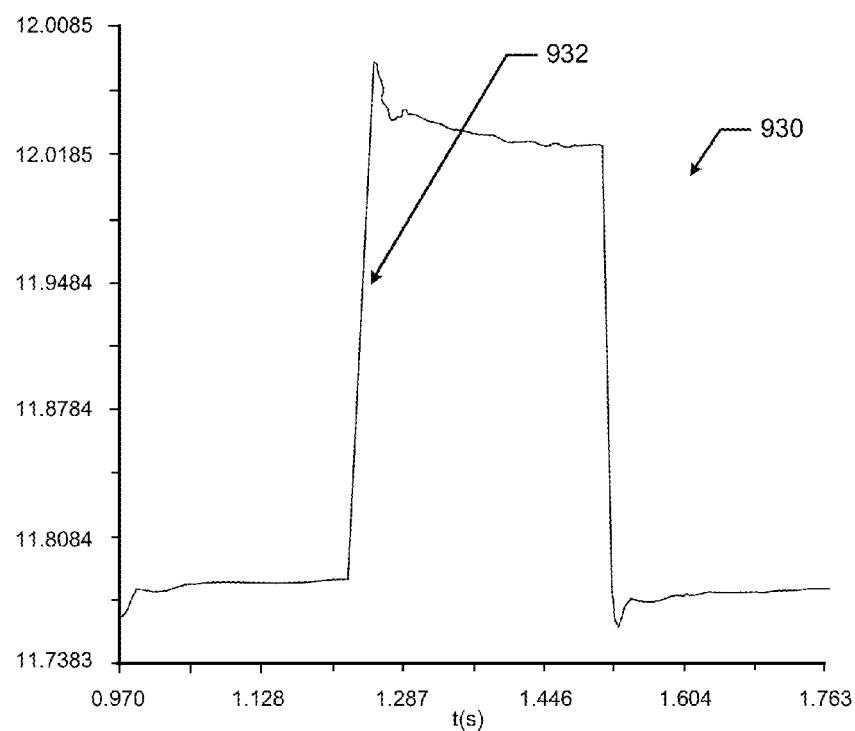
FIG. 10D is a graph depicting a square wave pulse according to one aspect.

Preferably, each square wave pulse period is shaped to minimize the positive and negative rise/fall times. For example, the transition intervals of each pulse's leading or trailing edges between each pulse may be tuned to create harmonics of $1.7\pm0.5$ Hz, $5.5\pm0.5$ Hz, $9.0\pm0.5$ Hz, $12.5\pm0.5$ Hz, and $16.5\pm0.5$ Hz. It is desired that the therapy waveform have minimal ringing or flutter at the square wave peaks, in order to be perceived as "clean" square waves. As the therapy pulse profiles may be modified in the amplitude and frequency domains, a power spectrum analysis shows that the preferred therapy waveform generates displacement of the pacifier 810 at a fundamental frequency of approximately 1.7 Hz and higher orders. This fundamental frequency is preferred to entrain the patient's nervous system through cutaneous signal detection. Further, the preferred therapy waveform has a Q factor greater than or equal to ½. As such, the relative high frequency of the rising and falling edges of the therapy pulse helps to achieve stimulus salience in the patient. During a therapy session, the surface of the pacifier 810 may experience one or more positive displacements, one or more negative displacements, or combinations thereof, including but not limited to alternating between positive and negative displacements. A therapeutic burst 928 having square wave pulses to cause only positive displacement of a pacifier surface is shown in FIG. 10C. Similarly, FIG. 10D depicts a single square wave pulse 930 having a rapid rise time, indicated generally as 934, of approximately 0.017 ms. The rapid rise times of the square wave pulse, which are typically less than about 190 ms and particularly those less than about 50 ms, are significantly more effective than low-velocity stimulus patterns having rise/fall times of approximately 190 ms or greater in providing patients with a beneficial and salient neurotherapy.

In all aspects, the number of square wave pulses per therapeutic burst, the number of therapeutic bursts per therapy session, and the amplitude of the square wave pulses are configurable by the user to account for variability in the patient. For example, the age, endurance, and/or aptitude of the patient may vary, thereby requiring the user to select or modify a therapy pulse profile via the therapy configuration submodule 600.

Figure 10E:
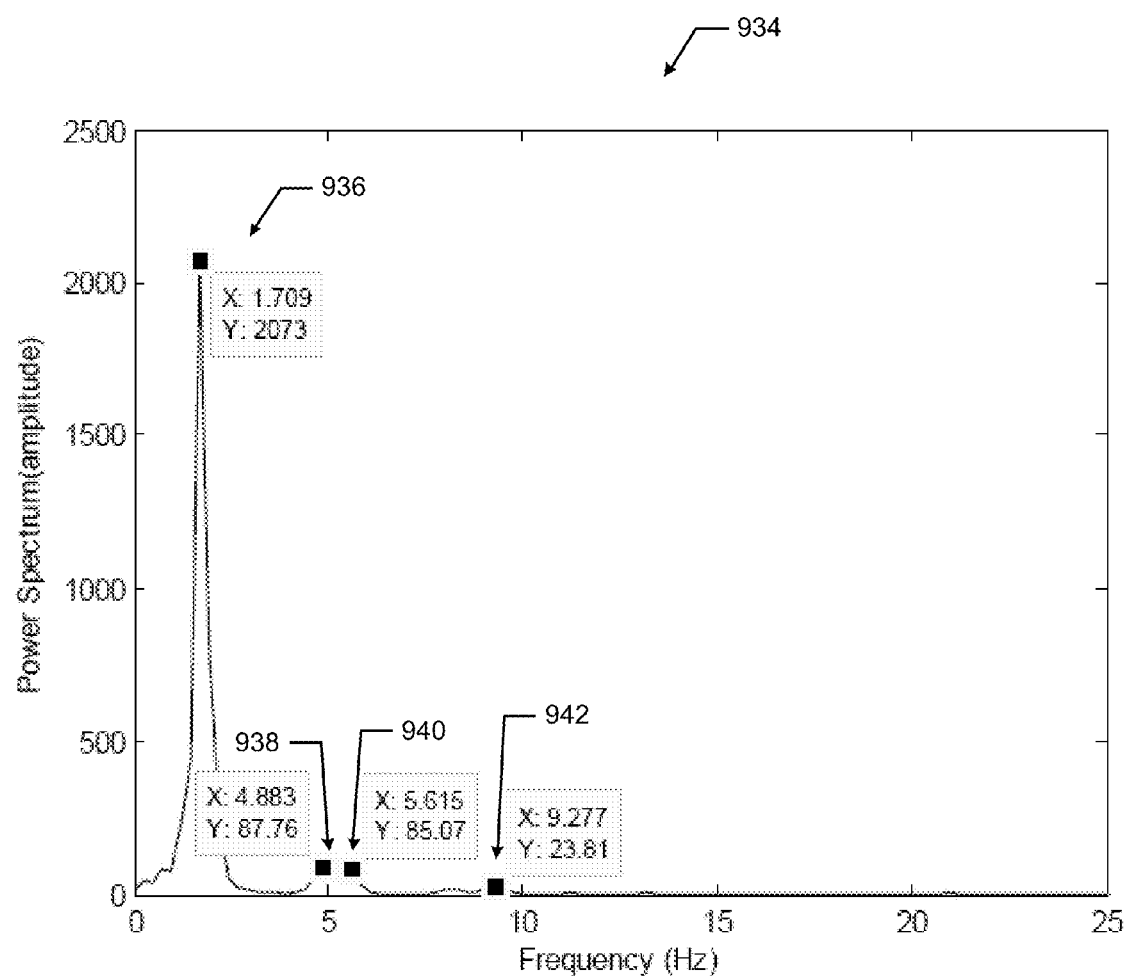
FIG. 10E is a graph depicting a power spectrum of a square wave pulse according to one aspect.

By way of example and not limitation, FIG. 10E depicts a power spectrum 934 of one exemplary square wave pulse. As shown, a fundamental frequency of approximately 1.709 Hz is generally indicated as 936. In contrast to lower velocity pulses, the square wave pulse includes several harmonics, generally indicated as 938-942, that transfer energy at approximately 4.883, 5.615, and 9.277 Hz, respectively. The additional high frequency components 938-942 present in the square wave pulse contribute significantly to its tactile signature as a higher velocity signal.

FIGS. 10F-I illustrate the adjusted means and standard errors resulting from a multivariate statistical analysis that compared the effectiveness of the high-velocity pulse (HVP) versus a low-velocity pulse (LVP) as they relate to four orofacial behaviors. FIGS. 10F-I depict the combined adjusted means for a control group, a group exposed to LVPs (LVP group), and a grouped exposed to HVPs (HVP group). Each of the groups used in the analysis were composed of four clinical sub-groups of preterm infants, including healthy infants, infants having respiratory distress syndrome, infants having chronic lung disease, and infants with diabetic mothers.

Figure 10F:
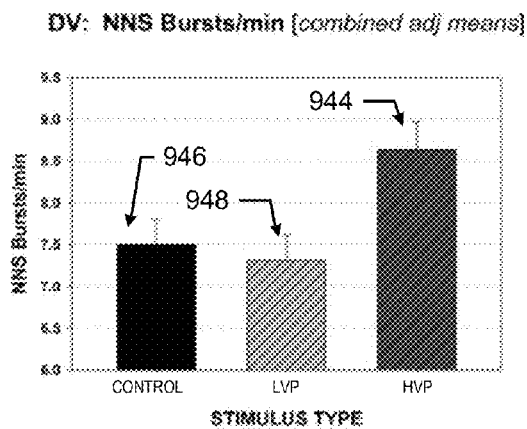
FIGS. 10F-I depict the results of analysis comparing the effects of various pulses as they relate to orofacial behaviors.
Figure 10G:
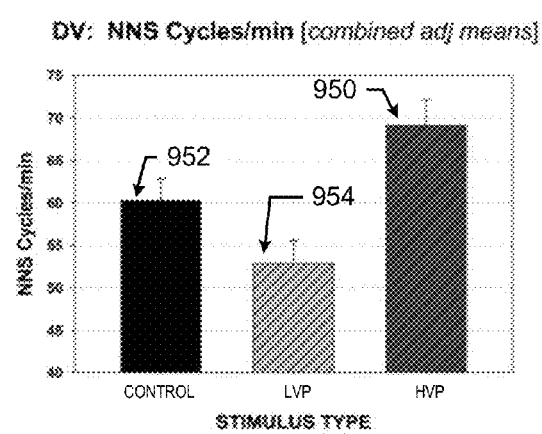
Figure 10H:
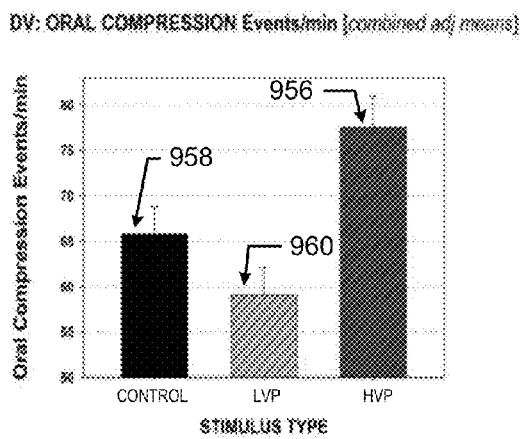
Figure 10I:
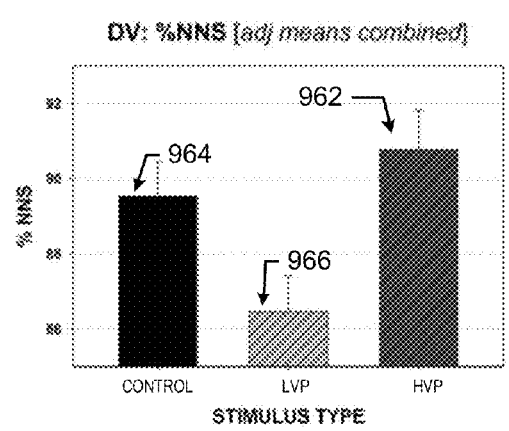

In particular, FIG. 10F illustrates that the HVP group, as indicated by 944, generated a greater number of NNS bursts per minute than the control group, as indicated by 946, and the LVP group, as indicated by 948. Similarly, FIG. 10G illustrates that the HVP group, as indicated by 950, generated a greater number of NNS cycles per minute than the control group, as indicated by 952, or the LVP group, as indicated by 954. FIG. 10H illustrates that the HVP group, as indicated by 956, generated a greater number of oral compression events per minute than the control group, as indicated by 958, or the LVP group, as indicated by 960. Likewise, FIG. 10I illustrates that the HVP group, as indicated by 962, generated a higher absolute percentage of NNS events relative to the total oral compressions per minute than the control group, as indicated by 964, or the LVP group, as indicated by 966. As shown, the HVP group exceeded the control group and the LVP group, thus indicating that the HVP is providing a greater neurotherapeutic benefit to the collective group of preterm infants. Further, within each HVP group, the infants having respiratory distress syndrome, infants having chronic lung disease, and infants with diabetic mothers benefited more from the HVP stimulus than did the healthy infants.

Methods of Using the Non-Nutritive/Nutritive Suck Entrainment System (Entrainment System)

Figure 11A:
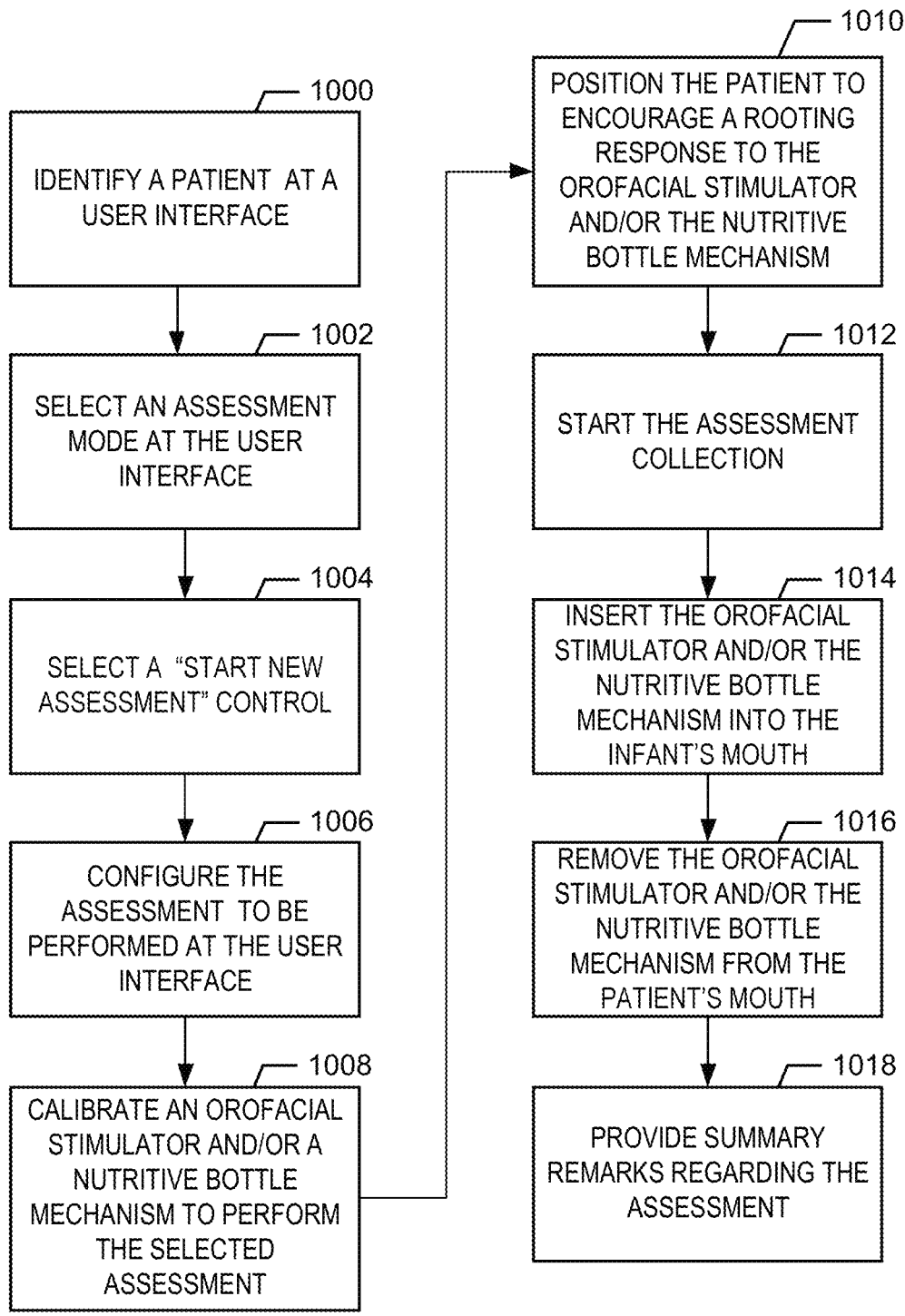
FIG. 11A illustrates a method for assessing a non-nutritive suck pattern or nutritive suck pattern according to one aspect of the therapeutic stimulus system.

FIG. 11A illustrates a method for performing an assessment session to capture and analyze a patient's NNS pattern or NS pattern in accordance with an aspect of the therapeutic stimulus system 100. At step 1000, a user of the therapeutic stimulus system 100 selects a patient from a displayed list of patients. The user then selects a control button to enter the assessment mode of the NNS/NS application 204 at step 1002 and selects the "start new assessment" control button 1224 at step 1004. The assessment session is configured as desired at step 1006 based upon the patient's age, injury, or other patient data 702 and optionally, data 704 regarding the patient's assessment history. The orofacial stimulator appliance 108 and/or the nutritive bottle mechanism 110 are calibrated at step 1008, while the patient is positioned to encourage a rooting response to the orofacial stimulator appliance 108 and/or the nutritive bottle mechanism 110 at step 1010. At step 1012, the assessment session is started, while the orofacial stimulator appliance 108 and/or the nutritive bottle mechanism 110 is contacted with the patient's lips and mouth at step 1014. In other aspects, the orofacial stimulator appliance 108 and/or the nutritive bottle mechanism 110 is inserted into the patient's mouth at step 1014. Similarly, in other aspects, the steps 1012 and 1014 may be reversed.

Once the assessment session is completed, the orofacial stimulator appliance 108 and/or the nutritive bottle mechanism 110 are removed from the patient at step 1016. After the feature extraction submodule 406 analyzes the collected assessment data, using the input form 1274 generated by the post-assessment review module 508. After the assessment session, the user may initiate another assessment session for the same patient or a different patient. Alternatively, the user may instead exit the NNS/NS application 204.

Figure 11B:
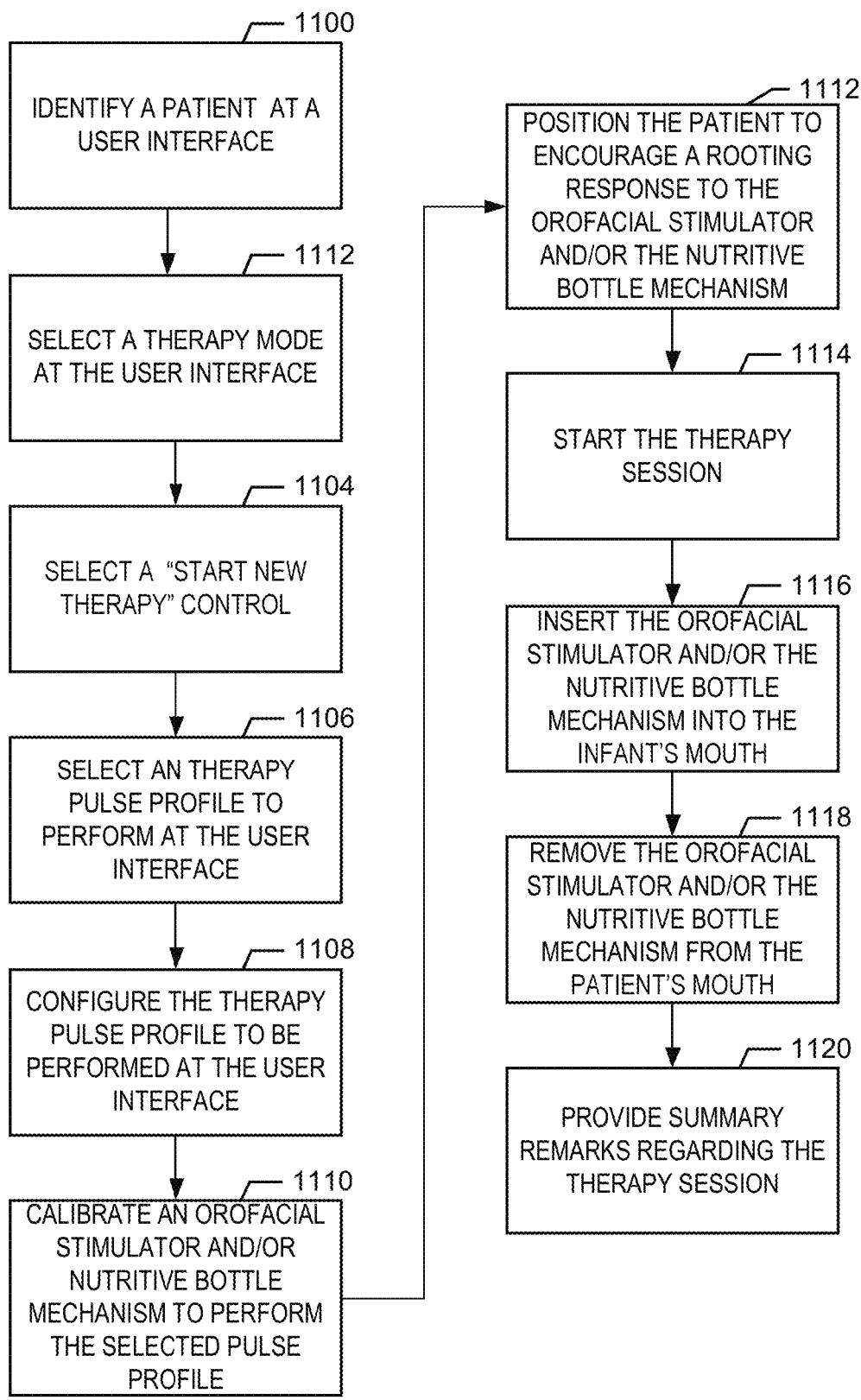
FIG. 11B illustrates a method for stimulating a patient to entrain an organized non-nutritive suck pattern or nutritive suck pattern according to one aspect of the therapeutic stimulus system.

FIG. 11B illustrates a method for performing a therapy session to entrain a patient's sCPG to generate an organized NNS pattern or organized NS pattern in accordance with an aspect of the therapeutic stimulus system 100. At step 1110, a user of the therapeutic stimulus system 100 selects a patient from a list of patients. The user then selects a control button to enter the therapy mode of the NNS/NS application 204 at step 1102 and selects a "start new therapy" control button 1278 at step 1104. The therapy pulse profile to be generated during the therapy session is selected from the therapy pulse profile data 708 at step 1106 and at step 1108, the therapy pulse profile is configured as desired based upon the patient's age, injury, or other patient data 702 and any of the patient's NNS/NS assessment data 704. The orofacial stimulator appliance 108 and/or the nutritive bottle mechanism 110 are calibrated at step 1110, while the patient is positioned to encourage a rooting response to the orofacial stimulator appliance at step 1112. At step 1114, the therapy session is started, while the orofacial stimulator appliance 108 and/or the nutritive bottle mechanism 110 is contacted with the patient's lips and mouth at step 1116. In other aspects, the orofacial stimulator appliance 108 and/or the nutritive bottle mechanism 110 is inserted into the patient's mouth at step 1116. Similarly, in other aspects, the steps 1114 and 1116 may be reversed. During the therapy session, the user may attempt to hold the patient as still as possible.

Once the therapy session is completed, the orofacial stimulator appliance 108 and/or the nutritive bottle mechanism 110 are removed from the patient at step 1118. The user may provide summary remarks regarding the therapy session at step 1120 using the GUI input form 1274 generated by the post-therapy review module 606. After the therapy session, the user may initiate another therapy session for the same patient or a different patient. Alternatively, the user may instead exit the NNS/NS application 204.

Exemplary Methods of Use by a Medical Professional to Treat an Individual with Impaired Neural Function An exemplary method of using the therapeutic stimulus system 100 by a medical professional to treat a patient having impaired neural function includes an initial step of powering on the various components of the NNS/NS therapeutic stimulus system 100, including the pulse generation system 106 and the computing device 102. Optionally, the user may verify that a back-up power supply, such as a battery, is properly connected, such that the use of the NNS/NS therapeutic stimulus system 100 will not be compromised by a loss of power.

After accessing the computing device and executing the NNS/NS application 204, the user logs in to the NNS/NS application 204, by selecting their username from a displayed list of approved usernames. The user then inputs their password to log in to the NNS/NS application 204. The medical professional may now access the records of an existing patient to perform an assessment or provide therapeutic stimulation. Alternately, the user may enter and save data regarding a new patient to the NNS/NS system 204.

To begin an assessment session, the user selects the patient's name in a displayed "Active Patient List". Next, the user selects "Assessment" to enter the assessment mode of the NNS/NS application 204. The user then selects a "Start New Assessment" control button and enters data into a displayed "Configuring Assessment" user interface. The user may enter, for example, the estimated minutes required for assessment and the color or type of pacifier to be used. After entering the data, the user continues and may select a displayed "Calibrate" control button, or depress the switch on the handpiece to automatically calibrate the system.

The user moves and positions the therapeutic stimulus system 100 near the patient and encourages the patient to take the pacifier 810 connected to or without the nutritive bottle mechanism 110 into their mouth. To begin the assessment session, the user presses the hand-piece button or selects a displayed "Start" control button, and gently places the pacifier 810 in the infant's mouth. During the session, the user may press the hand-piece button or a displayed "Pause/Resume" control button to pause the session. The assessment session will automatically stop when the designated time is complete, and the user may then gently remove the pacifier 810 from infant's mouth. To complete the assessment session, the user touches a "Close" control button, enters additional data in the displayed "Session summary" display, and finally concludes the session by selecting a "Done" control button.

To begin a therapy session, the user powers on the system and executes the NNS/NS application 204, similar to the steps of performing an assessment session. The user selects the patient's name in the displayed "Active Patient List". Next, the user selects "Therapy" to enter the therapy mode of the NNS/NS application 204. The user then selects a "Start New Therapy" control button and enters data into a displayed "Configuring Therapy" user interface. The user may select the type of therapy most appropriate for the patient. For example, the user may select a "Pre Oral Feed" control button to perform for a three minute therapeutic session prior to a patient's oral feeding. Conversely, the user may select "Gavage Feed" control button to provide therapeutic stimulus in combination with a non-oral feeding. As another example, the user may select a "Fixed Volume" control button to perform feeding session having a fixed volume of nutritive bolus. After selecting the therapy type, the user continues and may select a displayed "Calibrate" control button, or depress the switch on the handpiece to automatically calibrate the system.

The user moves and positions the therapeutic stimulus system near the patient and encourages the patient to take the pacifier with or without the nutritive bottle mechanism into their mouth. To begin the therapy session, the user presses the hand-piece button or selects a displayed "Start" control button, and gently places the pacifier in the infant's mouth. The user is reminded to hold the handpiece as still as possible during the therapy session. The therapy session will automatically stop when the designated time or therapy protocol is complete, and the user may then gently remove the pacifier from infant's mouth. To complete the assessment session, the user touches a "Close" control button, enters additional data in the displayed "Session summary" display, and finally concludes the session by selecting a "Done" control button.

Exemplary Methods of Use by a Medical Professional to Treat an Infant

An exemplary method of using the therapeutic stimulus system 100 by a medical professional to treat an infant having a deficient NNS pattern or NS pattern includes an initial step of powering on the various components of the NNS/NS therapeutic stimulus system 100, including the pulse generation system 106 and the computing device 102. Optionally, the user may verify that a back-up power supply, such as a battery, is properly connected, such that the use of the NNS/NS therapeutic stimulus system 100 will not be compromised by a loss of power.

After accessing the computing device and executing the NNS/NS application 204, the user logs in to the NNS application 204, by selecting their username from a displayed list of approved usernames. The user then inputs their password to log in to the NNS/NS application 204. The medical professional may now access the records of an existing patient to perform an assessment or provide therapeutic stimulation. Alternately, the user may enter and save data regarding a new patient to the NNS/NS system 204.

To begin an assessment session, the user selects the patient's name in a displayed "Active Patient List". Next, the user selects "Assessment" to enter the assessment mode of the NNS/NS application 204. The user then selects a "Start New Assessment" control button and enters data into a displayed "Configuring Assessment" user interface. The user may enter, for example, the estimated minutes required for assessment and the color or type of pacifier to be used. After entering the data, the user continues and may select a displayed "Calibrate" control button, or depress the switch on the handpiece to automatically calibrate the system.

The user positions the swaddled infant in a relaxed position or a feeding position and encourages a rooting response to the pacifier. To begin the assessment session, the user presses the hand-piece button or selects a displayed "Start" control button, and gently places the pacifier in the infant's mouth. During the session, the user may press the hand-piece button or a displayed "Pause/Resume" control button to pause the session. The assessment session will automatically stop when the designated time is complete, and the user may then gently remove the pacifier from infant's mouth. To complete the assessment session, the user touches a "Close" control button, enters additional data in the displayed "Session summary" display, and finally concludes the session by selecting a "Done" control button.

To begin a therapy session, the user powers on the system 100 and executes the NNS/NS application 204, similar to the steps of performing an assessment session. The user selects the patient's name in the displayed "Active Patient List". Next, the user selects "Therapy" to enter the therapy mode of the NNS/NS application 204. The user then selects a "Start New Therapy" control button and enters data into a displayed "Configuring Therapy" user interface. The user may select the type of therapy most appropriate for the patient. For example, the user may select a "Pre Oral Feed" control button to perform for a three minute therapeutic session prior to a patient's oral feeding. Conversely, the user may select "Gavage Feed" control button to provide therapeutic stimulus in combination with a non-oral feeding. As another example, the user may select a "Fixed Volume" control button to perform feeding session having a fixed volume of nutritive bolus. After selecting the therapy type, the user continues and may select a displayed "Calibrate" control button, or depress the switch on the handpiece to automatically calibrate the system.

The user positions the swaddled infant in a relaxed position or a feeding position, as necessary, and encourages a rooting response to the pacifier. To being the therapy session, the user presses the hand-piece button or selects a displayed "Start" control button, and gently places the pacifier in the infant's mouth. The user is reminded to hold the handpiece as still as possible during the therapy session. The therapy session will automatically stop when the designated time or therapy protocol is complete, and the user may then gently remove the pacifier from the infant's mouth. To complete the assessment session, the user touches a "Close" control button, enters additional data in the displayed "Session summary" display, and finally concludes the session by selecting a "Done" control button.

The method may also be performed on patients other than infants. The method is substantially the same; however the patient is clothed and positioned as appropriate for the patient's age, physical condition, or any other factor deemed relevant to the patient's care.

In the present disclosure, the methods disclosed may be implemented as sets of instructions or software readable by a device. Further, it is understood that the specific order or hierarchy of steps in the methods disclosed are instances of example approaches. Based upon design preferences, it is understood that the specific order or hierarchy of steps in the method can be rearranged while remaining within the disclosed subject matter. The accompanying method claims present elements of the various steps in a sample order, and are not necessarily meant to be limited to the specific order or hierarchy presented.

The described disclosure may be provided as a computer program product, or software, that may include a non-transitory machine-readable medium having stored thereon executable instructions, which are executed by one or more processors, and may be used to program a computer system (or other electronic devices) to perform a process according to the present disclosure. A non-transitory machine-readable medium includes any mechanism for storing information in a form (e.g., software, processing application) readable by a machine (e.g., a computer). The non-transitory machine-readable medium may include, but is not limited to, magnetic storage medium (e.g., floppy diskette), optical storage medium (e.g., CD-ROM); magneto-optical storage medium, read only memory (ROM); random access memory (RAM); erasable programmable memory (e.g., EPROM and EEPROM); flash memory; or other types of medium suitable for storing electronic executable instructions.

It is believed that the present disclosure and many of its attendant advantages will be understood by the foregoing description, and it will be apparent that various changes may be made in the form, construction, and arrangement of the components without departing from the disclosed subject matter or without sacrificing all of its material advantages. The form described is merely explanatory, and it is the intention of the following claims to encompass and include such changes.

While the present disclosure has been described with reference to various embodiments, it will be understood that these embodiments are illustrative and that the scope of the disclosure is not limited to them. Many variations, modifications, additions, and improvements are possible. More generally, embodiments in accordance with the present disclosure have been described in the context of particular implementations. Functionality may be separated or combined in blocks differently in various embodiments of the disclosure or described with different terminology. These and other variations, modifications, additions, and improvements may fall within the scope of the disclosure as defined in the claims that follow.

What is claimed is:

1. A system for improving an oral feeding ability of a patient, the system comprising:
   an assessment device to contact a patient and collect data related to an oral feeding ability of the patient;
   a computing device containing a processor to execute an assessment and therapy application; and
   the assessment and therapy application to:
   receive the data related to the oral feeding ability;
   predict one or more areas of neurological muscle activity that need further development while receiving the data related to the oral feeding ability;

wherein the assessment device determines that the patient has one of a weak NNS suck pressure less than or equal to ten cmH2O and an appropriate NNS suck pressure in a range of fifteen-twenty cmH2O; and develop a neurological therapy treatment for improving the one or more areas of neurological muscle activity that need further development.

2. The system of claim 1, wherein the oral feeding ability is improved by prophylactic feeding, wherein the assessment application determines a burst profile based on a pulse generated by the patient to reinforce a non-nutritive suck.

3. The system of claim 2, wherein the assessment application is in an "always on" mode of operation.

4. The system of claim 1, wherein the oral feeding ability is improved by "Reactive" pulse training, wherein the system analyzes a patient performance during a therapy stimulus and a moderate stimulus.

5. The system of claim 4 wherein the system assesses and develops a therapy for treating a sucking action and a swallowing action of the patient, the system further comprising:

a nutritive bottle mechanism to provide a nutritive bolus to the patient; and a transducer to detect the swallowing action of the patient.

6. The system of claim 5, wherein the bolus has a fixed-volume.

7. The system of claim 5, wherein the system further assess patient breathing and simulates breast feeding, the system further comprising an adaptive-flow fluid pump to mimic a flow of breast milk, wherein the pump varies and adapts a volume of the bolus as a function of patient effort.

8. The system of claim 7, wherein the patient effort is defined by a pressure and a nutritive suck activity of the patient, such that the patient must exert greater effort to increase the volume of the bolus.

9. The system of claim 1, wherein the one or more areas of neurological muscle activity that need further development include a regularity and number of individual sucks in individual non-nutritive suck (NNS) bursts, an organization of collective suck bursts, an intensity of effort, and an absence of NNS activity.

10. A method for improving an oral feeding ability of a patient, the method comprising:

contacting a patient with an assessment device to collect data related to an oral feeding ability of the patient;

executing an assessment and therapy application on a processor of a computing device in communication with the assessment device; and at the assessment and therapy application executing on the processor:

receiving the data related to the oral feeding ability; the assessment and therapy application executing on the processor determining that the patient has one of a weak NNS suck pressure less than or equal to ten cmH2O and an appropriate NNS suck pressure in a range of fifteen-twenty cmH2O;

predicting one or more areas of neurological muscle activity that need further development while receiving the data related to the oral feeding ability; and developing a neurological therapy treatment for improving the one or more areas of neurological muscle activity that need further development.

11. The method of claim 10, further comprising improving the oral feeding ability by prophylactic feeding by:

determining a burst profile based on a pulse generated by the patient to reinforce a non-nutritive suck, at the assessment application.

12. The method of claim 11, wherein the assessment application is in an "always on" mode of operation.

13. The method of claim 10, further comprising:

improving the oral feeding by "Reactive" pulse training; and analyzing a patient performance during a therapy stimulus and a moderate stimulus.

14. The method of claim 13, further comprising assessing and developing a therapy for treating a sucking action and a swallowing action of the patient by:

providing a nutritive bolus to the patient with a nutritive bottle mechanism; and using a transducer to detect the swallowing action of the patient.

15. The method of claim 14, wherein the bolus has a fixed-volume.

16. The method of claim 15, further comprising assessing patient breathing and simulating breast feeding by:

an adaptive-flow fluid pump to mimic a flow of breast milk, wherein the pump varies and adapts a volume of the bolus as a function of patient effort.

17. The method of claim 16, wherein the patient effort is defined by a pressure and a nutritive suck activity of the patient, such that the patient must exert greater effort to increase the volume of the bolus.

18. The method of claim 10, wherein the one or more areas of neurological muscle activity that need further development include a regularity and number of individual sucks in individual non-nutritive suck (NNS) bursts, an organization of collective suck bursts, an intensity of effort, and an absence of NNS activity.

* * * * *